United States Patent [19] [11] 4,230,703
Suzuki et al. [45] Oct. 28, 1980

[54] 11-OXODIBENZ(B,E)AZEPINES

[75] Inventors: Yasushi Suzuki, Yokohama; Kunio Tsukamoto, Tokyo; Nobuyoshi Minami, Yokohama; Yukio Hasegawa; Tadaharu Watanabe, both of Kawasaki; Katsuhiko Miyasaka, Atsugi; Takashi Mikami, Tokyo; Satoshi Funakoshi, Kawasaki, all of Japan

[73] Assignee: Teikoku Hormone Mfg. Co., Ltd., Tokyo, Japan

[21] Appl. No.: 891,112

[22] Filed: Mar. 28, 1978

[30] Foreign Application Priority Data

Apr. 1, 1977 [JP] Japan .................................. 52-36065
Sep. 12, 1977 [JP] Japan ................................ 52-108744

[51] Int. Cl.³ .................... C07D 223/20; A61K 31/55
[52] U.S. Cl. ............................ 424/244; 260/239 DD; 260/340.9 R
[58] Field of Search ................ 260/239 DD, 340.9 R; 424/244

[56] References Cited

U.S. PATENT DOCUMENTS 3,153,652 10/1964 Drukker et al. ................. 260/239 D
3,624,075 11/1971 Fitzi et al. ....................... 260/239 D
3,993,757 11/1976 Freedman ......................... 424/244

FOREIGN PATENT DOCUMENTS

13785/67 8/1967 Japan.
719/43 11/1967 Japan.

OTHER PUBLICATIONS

Drukker et al., "J. of Heterocyclic Chem.," vol. 2, pp. 276-282 (1965).

Primary Examiner—Donald G. Daus
Assistant Examiner—D. B. Springer
Attorney, Agent, or Firm—Wenderoth, Lind & Ponack

[57] ABSTRACT

Compounds of the general formula

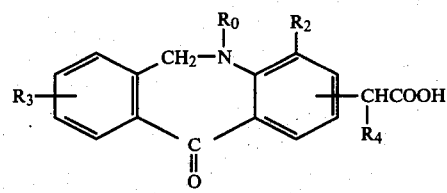

or their salts, esters or amide derivatives; and processes for their preparation. In the formula, $R_O$ represents hydrogen or lower alkyl, $R_2$ represents hydrogen, halogen or nitro, $R_3$ represents hydrogen or halogen, and $R_4$ represents hydrogen or lower alkyl; and when $R_O$ is hydrogen, $R_2$, $R_3$ and $R_4$ are all hydrogens and the group

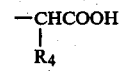

is present at the 2-position. These compounds exhibit superior analgesic and/or anti-inflammatory actions with little gastrointestinal troubles.

30 Claims, No Drawings

11-OXODIBENZ(b,e)AZEPINES

This invention relates to novel 11-oxodibenz[b,e]azepine derivatives, and more specifically to 5,6-dihydro-11-oxodibenz[b,e]azepine-alkanoic acid derivatives, a process for preparing these derivatives, and analgesic and/or anti-inflammatory agents comprising these compounds as active ingredients.

Some compounds having a 5,6-dihydro-11-oxodibenz[b,e]azepine skeleton have already been reported, and for example, 5,6-dihydro-11-oxodibenz[b,e]azepine, 5,6-dihydro-5-methyl-11-oxodibenz[b,e]azepine, 5,6-dihydro-5-benzyl-11-oxodibenz[b,e]azepine, and 5,6-dihydro-2-chloro-11-oxodibenz[b,e]azepine are known [see A. E. Drukker et al., Journal of Heterocyclic Chemistry, Vol. 2, pages 276–282 (1965), and Japanese Patent Publications Nos. 13785/67 and 719/68]. These literature references report that these known compounds are useful as intermediates for the synthesis of 11-aminoalkylidene derivatives having psychopharmacological properties.

However, no 5,6-dihydro-11-oxodibenz[b,e]azepine-alkanoic acid derivative having an alkanoic group substituted on one of the benzene rings and having analgesic and/or anti-inflammatory activities has been reported so far.

It is an object of this invention to provide novel 5,6-dihydro-11-oxodibenz[b,e]azepine-alkanoic acid derivatives.

Another object of this invention is to provide novel 5,6-dihydro-11-oxodibenz[b,e]azepine-alkanoic acid derivatives having superior analgesic and/or anti-inflammatory activities.

Still another object of this invention is to provide a process for preparing these novel 5,6-dihydro-11-oxodibenz[b,e]azepine-alkanoic acid derivatives.

Yet another object of this invention is to provide analgesic and/or anti-inflammatory agents comprising these novel 5,6-dihydro-11-oxodibenz[b,e]azepine-alkanoic acid derivatives as active ingredients.

A further object of this invention is to provide novel intermediate compounds which are useful for the production of these novel 5,6-dihydro-11-oxodibenz[b,e]azepine-alkanoic acid derivatives.

Other objects and advantages of this invention will become apparent from the following description.

According to this invention, there are provided 5,6-dihydro-11-oxodibenz[b,e]azepine-alkanoic acid derivatives of the general formula.

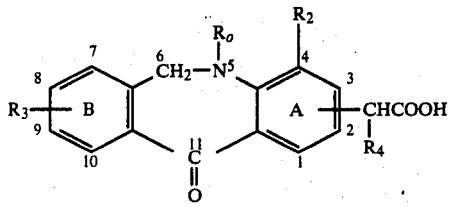

wherein $R_o$ represents a hydrogen atom or a lower alkyl group, $R_2$ represents a hydrogen or halogen atom or a nitro group, $R_3$ represents a hydrogen or halogen atom, and $R_4$ represents a hydrogen atom or a lower alkyl group; and when $R_o$ represents a hydrogen atom, $R_2$, $R_3$ and $R_4$ all represent a hydrogen atom, and the group

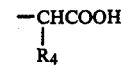

is present at the 2-position; or their salts, esters or amide derivatives.

Most of the compounds of formula (A) and their salts, esters and amide derivatives have superior analgesic and/or anti-inflammatory activities, and are useful as analgesic and anti-inflammatory agents. It is especially noteworthy that whilst many of conventional analgesic and anti-inflammatory agents typified by indomethacin, phenylbutazone and aspirin cause gastrointestinal troubles, the compounds of formula (A) and their salts, esters or amide derivatives do not show such side-effects.

In the present specification and the appended claims, the term "lower" means that groups modified by it have up to 6, preferably 1 to 4, carbon atoms.

Thus, in formula (A), the lower alkyl group denotes a linear or branched alkyl group having 1 to 6, preferably 1 to 4, carbon atoms, such as methyl, ethyl, n- or isopropyl, n-, iso-, sec- or tert-butyl, or n-pentyl. When $R_o$ in formula (A) represents a lower alkyl group, the alkyl group is preferably a linear alkyl group with 1 to 4 carbon atoms such as methyl, ethyl or n-propyl. When $R_4$ represents a lower alkyl group, the alkyl group may be either linear or branched, and is preferably a methyl group.

In the present specification and the appended claims, the term "halogen atom" denotes fluorine, chlorine, bromine and iodine, preferably chlorine and bromine.

Suitable substituents $R_2$ at the 4-position in formula (A) are hydrogen, chlorine, bromine and nitro, especially a hydrogen atom. The substituent $R_3$ on ring B is advantageously located at either the 8- or 9-position of the 5,6-dihydrodibenz[b,e]azepine ring, and a hydrogen, chlorine or bromine atom is especially suitable as $R_3$.

The alkanoic acid residue of formula

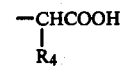

on ring A, which is most characteristic in the compound of formula (A), can be located at any of the 1-, 2- and 3-positions on the 5,6-dihydrodibenz[b,e]azepine ring when $R_o$ represents a lower alkyl group. From the standpoint of pharmacological activities it is desirably located at the 2- or 3-position, especially at the 2-position.

According to one embodiment of this invention, there are provided 5,6-dihydro-11-oxodibenz[b,e]azepines of the general formula

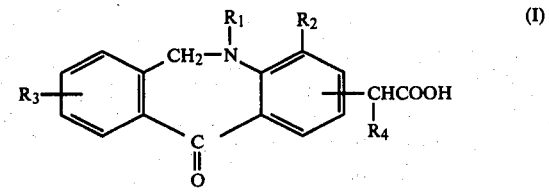

wherein $R_1$ represents a lower alkyl group, $R_2$ represents a hydrogen or halogen atom or a nitro group, $R_3$ represents a hydrogen or halogen atom, and $R_4$ represents a hydrogen atom or a lower alkyl group, and their salts, esters or amide derivatives.

A preferred group of compounds of formula (I) provided by this invention includes compounds of the following formula

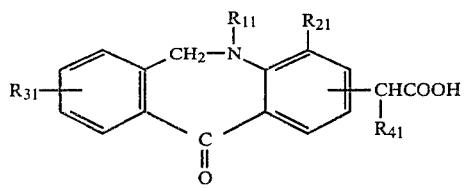

wherein $R_{11}$ represents an alkyl group containing 1 to 4 carbon atoms, $R_{21}$ represents a hydrogen, chlorine or bromine atom or a nitro group, $R_{31}$ represents a hydrogen, chlorine or bromine atom, and $R_{41}$ represents a hydrogen atom or a methyl group.

A more preferred group of compounds of formula (I) embraces compounds of the following formula

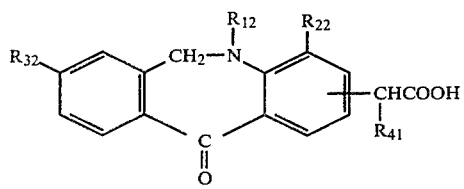

wherein $R_{12}$ represents a methyl, ethyl or n-propyl group, $R_{22}$ represents a hydrogen, chlorine or bromine atom, $R_{32}$ represents a hydrogen or chlorine atom, and $R_{41}$ represents a hydrogen atom or a methyl group.

The compounds of formula (I-b) and their salts, esters or amide derivatives have especially outstanding analgesic and/or anti-inflammatory activities, and are especially preferred.

Typical examples of the compounds of formula (I), (I-a), or (I-b) are listed below.

5,6-Dihydro-5-methyl-11-oxodibenz[b,e]azepine-1-acetic acid,
5,6-dihydro-5-methyl-11-oxodibenz[b,e]azepine-2-acetic acid,
5,6-dihydro-5-methyl-11-oxodibenz[b,e]azepine-3-acetic acid,
5,6-dihydro-5-ethyl-11-oxodibenz[b,e]azepine-1-acetic acid,
5,6-dihydro-5-ethyl-11-oxodibenz[b,e]azepine-2-acetic acid,
5,6-dihydro-5-ethyl-11-oxodibenz[b,e]azepine-3-acetic acid,
5,6-dihydro-5-n-propyl-11-oxodibenz[b,e]azepine-1-acetic acid,
5,6-dihydro-5-n-propyl-11-oxodibenz[b,e]azepine-2-acetic acid,
5,6-dihydro-5-n-propyl-11-oxodibenz[b,e]azepine-3-acetic acid,
5,6-dihydro-4-chloro-5-methyl-11-oxodibenz[b,e]azepine-2-acetic acid,
5,6-dihydro-4-bromo-5-methyl-11-oxodibenz[b,e]azepine-2-acetic acid,
5,6-dihydro-4-chloro-5-ethyl-11-oxodibenz[b,e]azepine-2-acetic acid,
5,6-dihydro-4-bromo-5-ethyl-11-oxodibenz[b,e]azepine-2-acetic acid,
5,6-dihydro-5-methyl-7-chloro-11-oxodibenz[b,e]azepine-2-acetic acid,
5,6-dihydro-5-methyl-8-chloro-11-oxodibenz[b,e]azepine-2-acetic acid,
5,6-dihydro-5-methyl-9-chloro-11-oxodibenz[b,e]azepine-2-acetic acid,
5,6-dihydro-5-methyl-10-chloro-11-oxodibenz[b,e]azepine-2-acetic acid,
5,6-dihydro-4-nitro-5-methyl-11-oxodibenz[b,e]azepine-2-acetic acid,
2-(5,6-dihydro-5-methyl-11-oxodibenz[b,e]azepin-1-yl)propionic acid,
2-(5,6-dihydro-5-methyl-11-oxodibenz[b,e]azepin-2-yl)propionic acid,
2-(5,6-dihydro-5-methyl-11-oxodibenz[b,e]azepin-3-yl)propionic acid,
2-(5,6-dihydro-5-ethyl-11-oxodibenz[b,e]azepin-1-yl)propionic acid,
2-(5,6-dihydro-5-ethyl-11-oxodibenz[b,e]azepin-2-yl)propionic acid,
2-(5,6-dihydro-5-ethyl-11-oxodibenz[b,e]azepin-3-yl)propionic acid,
2-(5,6-dihydro-5-n-propyl-11-oxodibenz[b,e]azepin-2-yl)propionic acid,
2-(5,6-dihydro-4-chloro-5-methyl-11-oxodibenz[b,e]azepin-2-yl)propionic acid,
2-(5,6-dihydro-4-bromo-5-methyl-11-oxodibenz[b,e]azepin-2-yl)propionic acid,
2-(5,6-dihydro-5-methyl-8-chloro-11-oxodibenz[b,e]azepin-2-yl)propionic acid,
2-(5,6-dihydro-4-chloro-5-ethyl-11-oxodibenz[b,e]azepin-2-yl)propionic acid,
2-(5,6-dihydro-4-bromo-5-ethyl-11-oxodibenz[b,e]azepin-2-yl)propionic acid,
2-(5,6-dihydro-5-ethyl-8-chloro-11-oxodibenz[b,e]azepin-2-yl)propionic acid,
2-(5,6-dihydro-4-nitro-5-ethyl-11-oxodibenz[b,e]azepin-2-yl)propionic acid,
2-(5,6-dihydro-5-methyl-11-oxodibenz[b,e]azepin-2-yl)butyric acid, and
2-(5,6-dihydro-5-ethyl-11-oxodibenz[b,e]azepin-2-yl)butyric acid.

The compounds of formulae (I), (I-a) and (I-b) can be in the form of salts, esters or amide derivatives.

Examples of the salts are alkali metal salts such as sodium, potassium or lithium salts; alkaline earth metal salts such as calcium or magnesium salts; salts with other metals such as aluminum salts; salts with aliphatic or alicylic amines such as diethylamine, triethylamine or dicyclohexylamine salts; salts with saturated heterocyclic amines such as pyrrolidine, piperidine or morpholine salts; salts with unsaturated heterocyclic amines such as pyridine or picoline salts; salts with organic bases such as brucine or morphine salts; and ammonium salts. Those which are pharmaceutically acceptable are preferred.

Suitable esters of the compounds of formula (I) are expressed by the following formula

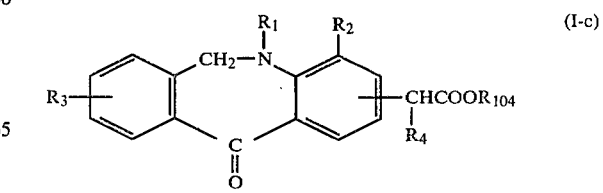

wherein R$_{104}$ represents a hydrocarbon group optionally having a substituent, and R$_1$, R$_2$, R$_3$ and R$_4$ are as defined above.

Suitable hydrocarbon groups expressed by R$_{104}$ in formula (I-c) are those containing up to 20, preferably 1 to 15 carbon atoms. Examples include lower alkyl groups such as methyl, ethyl, n- or iso-propyl, n-, iso-, sec- or tert-butyl; lower alkenyl groups such as allyl, cycloalkyl groups with 3 to 9 carbon atoms such as cyclopentyl or cyclohexyl; and aralkyl groups such as benzyl, phenethyl, diphenylmethyl or trityl. These groups may have at least one substituent. Specific examples of such substituents are a hydroxyl group, halogen atoms, lower alkoxy groups, ketal groups, and acetal groups. Specific examples of these hydrocarbon groups having a substituent include hydroxyethyl, hydroxypropyl, methoxyethyl, ethoxyethyl, 2,3-dihydroxypropyl, 2,2-dimethyl-1,3-dioxolan-5-yl methyl, 2,2-methylethyl-1,3-dioxolan-5-yl methyl, and sugar alcohol residues optionally ketalized.

Especially suitable esters of compounds (I) are lower alkyl esters, mono- or di-hydroxy-lower alkyl esters, lower alkoxy-lower alkyl esters, and ketalized polyhydroxy-lower alkyl esters.

Preferred amide derivatives of the compounds of formula (I) are those expressed by the following formula

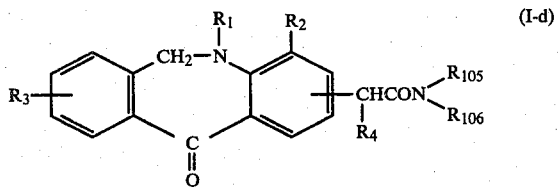

wherein R$_{105}$ and R$_{106}$, independently from each other, represent a hydrogen atom, a hydrocarbon group optionally having a substituent, a hydroxyl group or an amino group optionally having a substituent, or R$_{105}$ and R$_{106}$, taken together, represent a lower alkylene group which may have an oxygen, sulfur or nitrogen atom in the chain.

The hydrocarbon group optionally having a substituent in formula (I-d) may be the same as those exemplified above with regard to formula (I-c). Examples of the optionally substituted amino group include an amino group, mono(lower alkyl)amino groups, di(lower alkyl)amino groups, and a phenylamino group. When R$_{105}$ and R$_{106}$ together represent a lower alkylene group optionally containing an oxygen, sulfur or nitrogen atom in the chain, the group

specifically includes, for example, 5- or 6-membered heterocyclic groups such as pyrrolidino, piperidino, morpholino, 4-methylpiperazino or thiomorpholino.

Suitable amide derivatives of the compounds of formula (I) are lower alkylamides, hydroxy lower alkylamides, and hydroxyamides.

Some typical examples of the salts, esters and amide derivatives of the compounds of formula (I) are given below. It should be understood that the present invention is not limited by the following specific exemplification, and any salts, esters and amide derivatives of the compounds of formula (I) are included within the scope of this invention.

Sodium 5,6-dihydro-5-methyl-11-oxodibenz[b,e]azepine-2-acetate,

2'-hydroxyethyl-5,6-dihydro-5-methyl-11-oxodibenz[b,e]azepine-2-acetate, 2,2-dimethyl-1,3-dioxolan-5-yl methyl 5,6-dihydro-5-methyl-11-oxodibenz[b,e]azepine-2-acetate, methyl 5,6-dihydro-5-methyl-11-oxodibenz[b,e]azepine-2-acetate, methyl 5,6-dihydro-5-ethyl-11-oxodibenz[b,e]azepine-2-acetate, methyl 5,6-dihydro-5-n-propyl-11-oxodibenz[b,e]azepine-2-acetohydroxamic acid, and 5,6-dihydro-5-methyl-11-oxodibenz[b,e]azepine-2-N-methyl acetamide.

According to another embodiment of this invention, there are provided a compound of formula

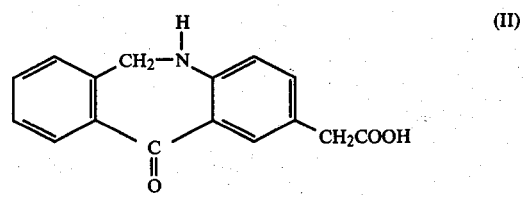

i.e. 5,6-dihydro-11-oxodibenz[b,e]azepine-2-acetic acid, and its salts or esters.

The compound of formula (II) and its salts or esters also have outstanding analgesic and anti-inflammatory activities which are higher than those of the compounds of formula (I-b). These are especially preferred compounds in this invention.

The salts of the compound of formula (II) may, for example, be the same salts as those given above with regard to formula (I).

Suitable esters of this compound are expressed by the following formula

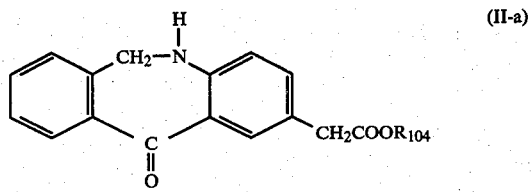

wherein R$_{104}$ is as defined above, and the lower alkyl esters are especially preferred.

Some examples of the salts and esters of the compound of formula (II) are methyl 5,6-dihydro-11-oxodibenz[b,e]azepine-2-acetate, ethyl 5,6-dihydro-11-oxodibenz[b,e]azepine-2-acetate, sodium 5,6-dihydro-11-oxodibenz[b,e]azepine-2-acetate, and aluminum 5,6-dihydro-11-oxodibenz[b,e]azepine-2-acetate. It should be understood that the invention is not limited to these examples, and any salts and esters of the compound of formula (II) are included within the scope of this invention.

According to one aspect of this invention, the compound of formula (I) or its salt, ester or amide derivative can be prepared by a process which comprises (a) cyclizing a compound of the general formula

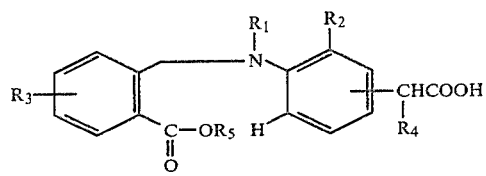 (III-1)

wherein $R_5$ represents a hydrogen atom, an alkali metal atom or a hydrocarbon group, and $R_1$, $R_2$, $R_3$ and $R_4$ are as defined above, or its salt, ester or amide derivative, or (b) when preparing a compound of formula (I) in which $R_4$ represents a lower alkyl group and $R_1$, $R_2$ and $R_3$ are as defined above, reacting a compound of the formula

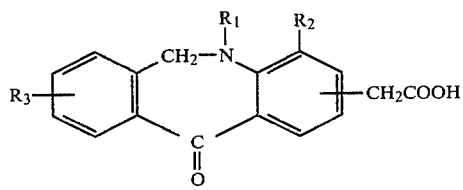 (I-e)

wherein $R_1$, $R_2$ and $R_3$ are as defined above, or its salt, ester or amide derivative with a lower-alkylating agent, or (c) when preparing a compound of formula (I) in which $R_2$ represents a halogen atom or a nitro group, and $R_1$, $R_3$ and $R_4$ are as defined above, halogenating or nitrating a compound of the formula

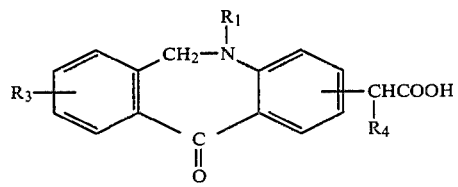 (I-f)

wherein $R_1$, $R_3$ and $R_4$ are as defined above, or its salt, ester or amide derivative, or (d) treating a compound of the formula

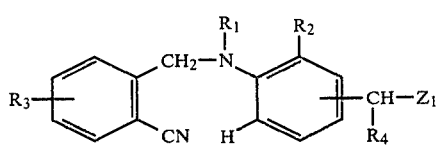 (III-2)

wherein $Z_1$ represents a carboxyl group or its salt, ester or amide derivative, or a group which can be converted to a carboxyl group or its salt, ester or amide derivative by hydrolysis, and $R_1$, $R_2$, $R_3$ and $R_4$ are as defined above, with polyphosphoric acid or its ester and then with water, or (e) hydrolyzing or subjecting to alcoholysis a compound of the formula

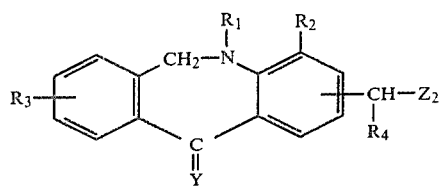 (IV)

wherein Y represents an oxygen atom or the group $=NR_6$ in which $R_6$ represents a hydrogen atom or a hydrocarbon group, or the group $$\left(\begin{array}{c} OR_7 \\ \\ OR_8 \end{array}\right)$$

in which $R_7$ and $R_8$, independently from each other, represent a lower alkyl group, or together represent a lower alkylene group, $Z_2$ represents a carboxyl group or its salt, ester or amide derivative or a group convertible to a carboxyl group or its salt, ester or amide derivative by hydrolysis or alcoholysis, and $R_1$, $R_2$, $R_3$ and $R_4$ are as defined above, and when Y is an oxygen atom, $Z_2$ does not represent a carboxyl group or its salt, ester or amide derivative, or (f) converting the group $X_1$ in a compound of the formula

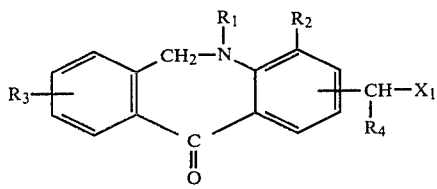 (V)

wherein $X_1$ represents a halogen atom and $R_1$, $R_2$, $R_3$ and $R_4$ are as defined above, to a carboxyl group or its salt, ester or amide derivative, or (g) when preparing a compound of formula (I) in which the group

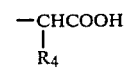

is located at the 2-position of the dibenz[b,e]azepine ring, $R_4$ is a hydrogen atom and $R_1$, $R_2$ and $R_3$ are as defined above, treating a compound of the formula

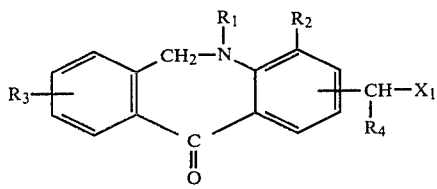 (VI)

wherein $R_1$, $R_2$ and $R_3$ are as defined above, ith ammonia or a primary or secondary amine in the presence of sulfur and then hydrolyzing the treated product, or (h) when preparing a compound of formula (I) in which the group

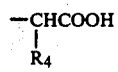

is located at the 2-position of the dibenz[b,e]azepine ring, $R_4$ is a hydrogen atom, and $R_1$, $R_2$ and $R_3$ are as defined above, reacting a compound of the formula

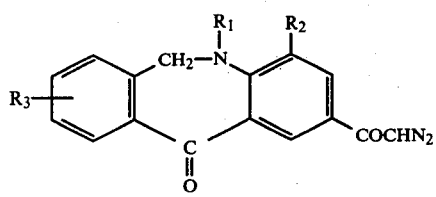

(VII)

wherein $R_1$, $R_2$ and $R_3$ are as defined above, with water or an alcohol, and (i) if desired, converting the resulting compound of formula (I) to its salt, ester or amide derivative, or if further desired, converting the salt or ester of the compound of formula (I) to the corresponding amide derivative, or if desired, converting the resulting salt, ester or amide derivative of the compound of formula (I) to the free acid of formula (I).

Cyclization of the compound of formula (III-1) shown in procedure (a) above can be carried out in the presence or absence of an inert solvent. Examples of the inert solvent that may be used in this reaction are halogenated hydrocarbons such as methylene chloride, chloroform, carbon tetrachloride or tetrachloroethane; nitrobenzene; and carbon disulfide.

The temperature for the cyclization is not critical, and can be varied over a wide range depending upon the type of the compound of formula (III-1). The cyclization can be performed even at room temperature, but generally can be promoted by heating. The upper limit of the heating temperature differs depending upon the starting material used, but it may be the decomposition temperature of the starting material. Usually, temperatures of not more than 300° C. are desirable. More preferably, the temperature is 50° to 200° C., especially 80° to 150° C.

Advantageously, the cyclization reaction is continued for 0.5 to 30 hours, especially 1 to 5 hours, under these temperature conditions.

It has been found that according to this invention the cyclization of the compound of formula (III-1) or its salt, ester or amide derivative can be markedly promoted in the presence of a condensing agent in the reaction system. Examples of the condensing agent are polyphosphoric acid (including a mixture in any desired proportion of phosphorus pentoxide and phosphoric acid), organic esters of polyphosphoric acid (e.g., lower alkyl esters of polyphosphoric acid such as ethyl polyphosphate), conc. sulfuric acid, and Friedel-Crafts type condensing agents (e.g., anhydrous aluminum chloride, anhydrous tin chloride, anhydrous ferric chloride, or anhydrous zinc chloride). The "Friedel-Crafts type condensing agent" denotes a compound which can be an electron acceptor, such as a compound which will generate an acyl cation by extracting a halogen atom from an acid halide. Polyphosphoric acid and its organic acid esters produce an especially great effect of promoting the cyclization reaction, and are therefore preferred in this invention.

The amount of the condensing agent is not critical, and can be varied widely depending upon the types of the starting material and/or condensing agent used. For example, when polyphosphoric acid or its organic acid ester is used, the amount of the condensing agent is at least equal to the amount of the starting material of formula (III-1), usually 1.1 to 100 times the weight of the latter. If conc. sulfuric acid or a Friedel-Crafts type condensing agent is used, its amount is at least 1 equivalent, usually 1.1 to 10 equivalents, per mole of the starting material of formula (III-1).

When polyphosphoric acid, a polyphosphoric acid ester or sulfuric acid is used in a large excess, the condensing agent can concurrently act as a reaction solvent.

The cyclization reaction can, if desired, be carried out in an atmosphere of an inert gas such as a nitrogen or argon gas.

After the reaction, the desired product is recovered from the reaction mixture by a known method. For example, the reaction mixture is poured into a large quantity of cold water or ice, and the precipitated compound is collected by filtration or by extraction with an organic solvent. As required, the product can be purified by recrystallization, chromatography, etc.

The compounds of formula (III-1) and their salts, esters or amide derivatives used as the starting material in the cyclization in accordance with this invention are novel compounds not described heretofore in the literature. Among these, compounds of the following general formula

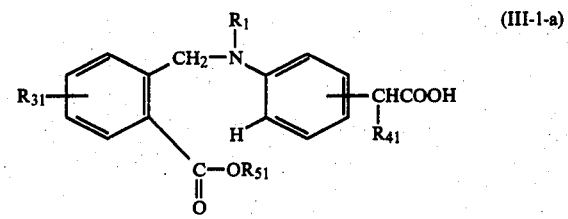

(III-1-a)

wherein $R_{11}$ represents an alkyl group with 1 to 4 carbon atoms, $R_{31}$ represents a hydrogen, chlorine or bromine atom, $R_{41}$ represents a hydrogen atom or a methyl group, and $R_{51}$ represents a hydrogen atom, an alkali metal or a lower alkyl group, and their salts, esters or amide derivatives are especially preferred. These compounds can be synthesized by the procedure shown in Reaction Scheme III below.

According to procedure (b) of this invention, the carboxymethyl group (—CH$_2$COOH) present at the 1-, 2- or 3-position of the compound of formula (I-e) can be converted to a 1-carboxyl-1-lower alkylmethyl group

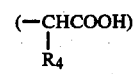

by reacting the compound of formula (I-e) or its salt, ester or amide derivative with a lower-alkylating agent.

The compounds of formula (I-e) used as the starting material in this alkylating reaction are embraced within the definition of formula (I), and can be produced by procedure (a) or by various other procedures to be described.

Any alkylating agents usually employed for alkylating the active carbon atoms of aliphatic hydrocarbons can be used as the lower-alkylating agent to be reacted with the compound of formula (I-e) or its salt, ester or amide derivative. Examples of suitable alkylating agents are lower alkyl halides such as methyl iodide, ethyl iodide and propyl iodide, and lower alkyl esters of sulfuric acid such as dimethyl sulfate and diethyl sulfate.

Desirably, one of the two hydrogen atoms at the methylene moiety of the carboxymethyl group should be activated or protected prior to alkylation by the method shown in the following reaction scheme, for example, so that only one of them may be easily and selectively alkylated. One example of this method is shown in the following Reaction Scheme I.

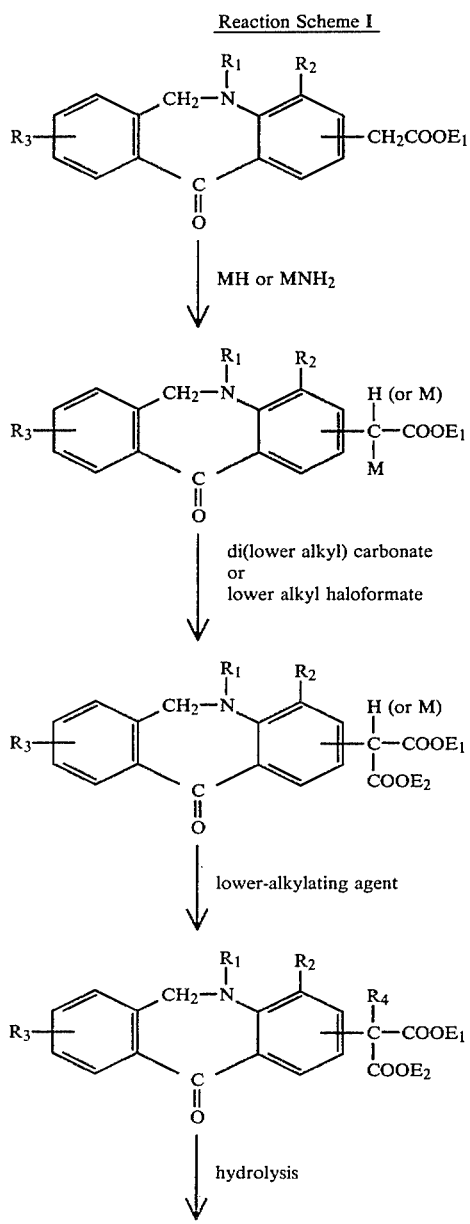

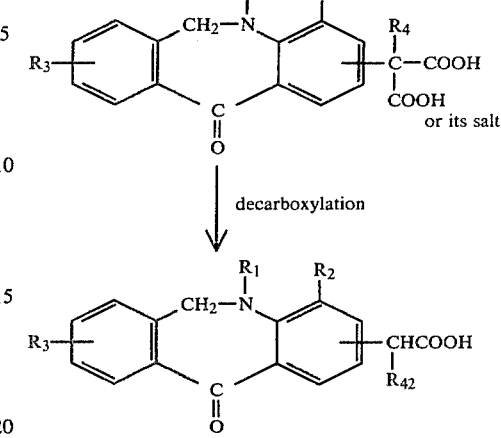

In each of the above formulae, $R_{42}$ represents a lower alkyl group, M represents an alkali metal such as sodium, potassium or lithium, $E_1$ represents an ester residue, $E_2$ represents a lower alkyl group, and $R_1$, $R_2$ and $R_3$ are as defined above.

Treatment of the compound of formula (I-e-1) with an alkali metal hydride or an alkali metal amide (for example, sodium hydride, potassium hydride, sodium amide, or potassium amide) and the subsequent treatment of the product with a di(lower alkyl) carbonate or a lower alkyl haloformate (such as dimethyl carbonate, diethyl carbonate, methyl chloroformate, ethyl chloroformate, isopropyl chloroformate, or isobutyl chloroformate) may be carried out stepwise. Usually, however, they are carried out in one step. Specifically, the compound of formula (I-e-1) can be converted to the compound of formula (I-e-3) by reacting it with a di(lower alkyl) carbonate or a lower alkyl haloformate in the presence of an alkali metal hydride or an alkali metal amide in a customary manner.

This reaction can be carried out either in the presence or absence of solvent. Examples of suitable solvents that may be used in the reaction are ethers such as diethyl ether, tetrahydrofuran, dioxane, dimethoxyethane or diethylene glycol dimethyl ether, sulfoxides such as dimethyl sulfoxide, and aromatic hydrocarbons such as benzene or toluene. The reaction temperature is usually from about 0° C. to the reflux temperature of the reaction mixture, preferably 5° to 180° C. Advantageously, the starting mixture is allowed to stand at room temperature for a while, and then reacted while it is heated to 50° to 150° C.

The resulting compound of formula (I-e-3) in which one of the hydrogen atoms at the methylene moiety of the carboxymethyl group is protected by an alkoxycarbonyl group (—COOE$_2$) can then be reacted with the lower-alkylating agent.

This alkylating reaction can also be carried out in the presence or absence of solvent. Usuable solvents are the same as those exemplified above. The alkylating temperature is not critical, and can be varied widely depending upon the type of the alkylating agent to be used. Generally, the suitable temperature is from room temperature to the reflux temperature of the reaction mixture, especially 50° to 150° C.

The amount of the lower alkylating is neither critical, and can be widely varied depending upon, for example, the type of the lower-alkylating agent or the reaction conditions. Generally, the amount of the alkylating agent is at least 1.0 mole, preferably 3 to 10 moles, per mole of the compound of formula (I-e-3).

The resulting alkylated product of formula (I-e-4) can be easily converted to a compound of formula (I-e-5) by hydrolysis, for example, by heating it in an organic solvent, water or a mixture of these in the presence of an aqueous solution of an alkali such as sodium hydroxide or an inorganic acid such as hydrochloric acid or sulfuric acid. Heating this compound usually in the absence of a solvent and in the presence or absence of an alkali, especially an alkali metal hydroxide such as sodium hydroxide or potassium hydroxide can yield the compound of formula (I-g) which is the compound of formula (I) in which $R_4$ is a lower alkyl group. The heating temperature at this time can be from the melting point of the compound of formula (I-e-5) to a temperature lower than the decomposition temperature of the compound of formula (I-g) when the reaction is performed in the absence of alkali. In the presence of alkali, heating can of course be performed at a temperature higher than the melting point, but generally, decarboxylation can be achieved by heating to a temperature lower than the melting point, for example to a temperature of 80° to 120° C.

In a series of the reactions shown in the Reaction Scheme I, the compound of formula (I-g) can also be prepared by causing the aforesaid lower-alkylating agent to act on a compound of the formula

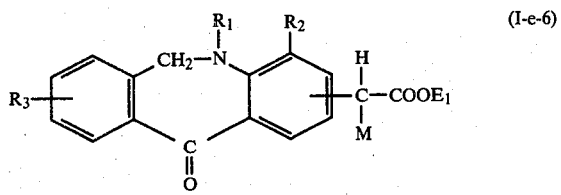

(I-e-6)

wherein $R_1$, $R_2$, $R_3$, $E_1$ and M are as defined above, which is advantageously obtained by reacting the compound of formula (I-e-1) with not more than 1 equivalent of an alkali metal hydride or an alkali metal amide per mole of the compound of formula (I-e-1).

Alkylation of the compound of formula (I-e-6) can be performed by reacting it with a lower-alkylating agent in the absence of solvent or in the presence of a solvent of the type exemplified above. The alkylating temperature is not critical, and can be varied widely depending upon the type of the alkylating agent used. Generally, it is suitably from −10° to the reflux temperature of the reaction mixture, preferably from 0° C. to 30° C. The amount of the alkylating agent is neither critical, and can be varied widely. Generally, the amount of the alkylating agent is at least 1 mole, preferably 3 to 10 moles, per mole of the compound of formula (I-e-6).

The resulting compound of formula (I-g) can be recovered from the reaction mixture in the manner to be described.

According to procedure (c) of this invention, a halogen atom or a nitro group can be introduced into the 4-position of the 5,6-dihydrodibenz[b,e]azepine ring by halogenating or nitrating a compound of formula (I) in which $R_2$ is a hydrogen atom, that is, a compound of the following formula

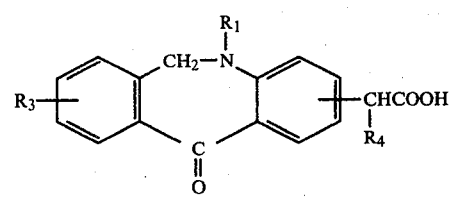

(I-f)

wherein $R_1$, $R_3$ and $R_4$ are as defined above, or its salt, ester or amide derivative.

Halogenation of the compound of formula (I-f) or its salt, ester or amide derivative can be performed by reacting it with a halogenating agent in the absence of a solvent, or in the presence of an inert organic solvent such as a halogenated aliphatic hydrocarbon (e.g., dichloromethane, chloroform, carbon tetrachloride or tetrachloroethane), or an ether (e.g., diethyl ether, tetrahydrofuran, dioxane, dimethoxyethane or ethylene glycol dimethyl ether).

Any halogenating agents frequently used for the halogenation of a benzene ring can be used in this invention. Examples of such a halogenating agent include molecular halogens (such as chlorine or bromine); N-halo-acid amides or N-halo-acid imides (such as N-bromoacetamide, N-chlorosuccinimide, N-bromosuccinimide, N-chlorophthalimide, N-bromophthalimide); halides of phosphorus-group elements such as phosphorus pentachloride, phosphorus pentabromide or antimony pentachloride; and adducts of iodine or iodinated aromatic hydrocarbons with chlorine (such as iodine chloride or iodobenzene dichloride). Of these, the molecular halogens and N-halo-succinimides are especially preferred.

The halogenation reaction using these halogenating agents can be performed under usual reaction conditions.

The amount of the halogenating agent to be used can be varied widely depending upon the type of the halogenating agent, etc. Usually, it is desirable to use it in a substantially equimolar amount to the compound of formula (I-f) used.

Nitration of the compound of formula (I-f) can be performed by treating it with a nitrating agent in the absence of a solvent, or in the presence of an inert organic solvent such as alkanoic acids (e.g., acetic acid or propionic acid), a mixture of acetic acid and conc. sulfuric acid, or an alkanoic acid anhydride (e.g., acetic anhydride or propionic anhydride). Sulfuric acid is also a suitable medium.

Any nitrating agents used for the nitration of a benzene ring can be used in this invention. Examples include conc. nitic acid, fuming nitric acid, a mixture of conc. nitric acid and conc. sulfuric acid (mixed acid), a mixture of conc. sulfuric acid and niter, a mixture of conc. sulfuric acid and Chile niter, a mixture of niter or Chile niter and acetic acid, and nitrogen pentoxide ($N_2O_5$). Nitration with a mixture of conc. sulfuric acid and niter using acetic acid as a solvent is especially preferred.

Nitration of the compound of formula (I-f) or its salt, ester or amide derivative with such a nitrating agent can be performed under known reaction conditions. The amount of the nitrating agent is not critical, but preferably, it is advantageous that the amount is substantially equivalent to one mole of the compound of formula (I-f).

Thus, the compound of formula (I) in which $R_2$ represents a halogen atom or a nitro group can be obtained in a good yield, and can be recovered from the reaction mixture in the manner described above.

According to procedure (d) of the present invention, the compound of formula (I) or its salt, ester or amide derivative can be obtained by treating a compound of the formula

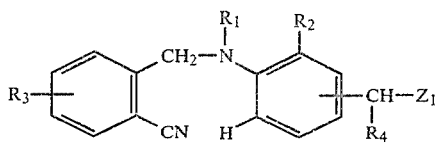
(III-2)

wherein $R_1$, $R_2$, $R_3$, $R_4$ and $Z_1$ are as defined above, with polyphosphoric acid or its ester and then with water.

Reaction of the compound of formula (III-2) with polyphosphoric acid or its ester can be performed in the absence of a solvent or in the presence of an inert organic solvent of the type exemplified above with regard to procedure (a). The reaction can be performed at room temperature, but generally heating can promote the reaction. The heating temperature is not critical, and can be varied widely depending upon the type of the compound of formula (III-2) used, etc. Generally, the suitable temperature is at least 50° C., preferably 80° to 200° C., more preferably 95° to 130° C.

The amount of polyphosphoric acid or its ester (e.g., ethyl ester) is neither critical, and can be varied over a wide range. Generally its amount is advantageously at least about one equivalent weight, preferably 1.1 to 100 equivalent weights, per mole of the compound of formula (III-2) or its salt, ester or amide derivative.

When polyphosphoric acid or its ester is used in excess, it acts not only as a condensing agent (cyclizing agent), but also as a reaction medium.

Preferably, this reaction is carried out in an atmosphere of an inert gas such as a nitrogen or argon gas.

It is thus presumed that in the reaction system, a compound of the following formula

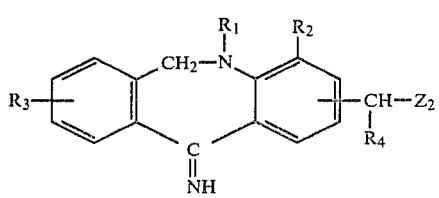
(IV-1)

wherein $R_1$, $R_2$, $R_3$, $R_4$ and $Z_2$ are as defined above, or its polyphosphoric acid adduct will be formed.

The compound of formula (I) or its salt, ester or amide derivative can be obtained in a good yield by mixing the resulting reaction mixture with a large amount of water or ice water and if required, heating the mixture to a temperature up to the boiling point of the reaction mixture.

The resulting product can be separated and/or purified in the same way as in the procedure (a) described above.

The compounds of formula (III-2) used as the starting material in procedure (d) are novel compounds not described heretofore in the literature, and can be prepared by the method shown in Reaction Scheme III given hereinbelow.

The carboxylic acid salt group expressed by $Z_1$ in formula (III-2) includes, for example, carboxyl groups in the form of salts such as a metal salt (e.g., an alkali metal, alkaline earth metal or aluminum salt), a salt with an aliphatic or alicyclic amine, a salt with an unsaturated heterocyclic amine, a salt with another organic base, or an ammonium salt. The carboxylate ester group can be expressed by the formula $-COOR_{104}$, and the carboxylic acid amide derivative group can be expressed by the formula

$R_{104}$, $R_{105}$ and $R_{106}$ are as defined hereinabove.

Examples of the group convertible to a carboxyl group or its salt, ester or amide derivative group by hydrolysis are a cyano group, unsubstituted or substituted hydrazide groups (for example, $-CONHNH_2$, $-CONHNHCH_3$, $-CONHNHC_2H_5$, $-CONHNHC_6H_5$, $-CONHN(CH_3)_2$,

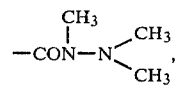

or

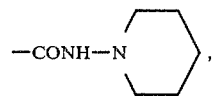

a residue of imide acid or its esters

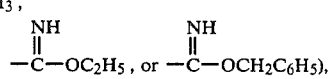

or an acid anhydride residue (e.g., $-COOCOCH_3$, $-COOCOC_2H_5$, or $-COOCOC_6H_5$), and an azide group ($-CON_3$). Of these, the cyano group and azide group are especially preferred.

According to procedure (e) of this invention, a compound of the following formula

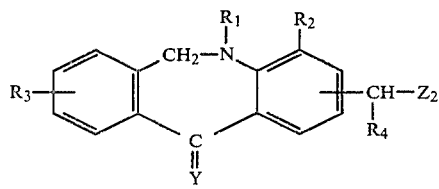
(IV)

wherein $R_1$, $R_2$, $R_3$, $R_4$, Y and $Z_2$ are as defined above, can be converted to the compound of formula (I) by hydrolysis or alcoholysis.

Hydrolysis of the compound of formula (IV) can be performed by using an aqueous solution of an alkali or an acid in the absence or presence of a water-miscible organic solvent, for example an alcohol such as methanol, ethanol or Cellosolve, a ketone such as acetone or methyl ethyl ketone, an ether such as tetrahydrofuran, dimethoxyethane or dioxane, or dimethyl sulfoxide. Its alcoholysis can be performed by using an alcohol in the presence of conc. sulfuric acid, hydrogen chloride gas, phosphoric acid, etc.

Examples of alkalies that can be used for the hydrolysis include alkali metal hydroxides such as sodium hydroxide or potassium hydroxide, alkaline earth metal hydroxides such as barium hydroxide, and alkali metal carbonates such as sodium carbonate or potassium carbonate. Examples of usable acids are hydrochloric acid, sulfuric acid, p-toluenesulfonic acid, phosphoric acid, and trifluoromethanesulfonic acid.

The acid or alkali can be used in an amount of usually at least 2 equivalents, preferably 5 to 50 equivalents, per mole of the compound of formula (IV).

Hydrolysis can be performed at a temperature of from 0° C. to the reflux temperature of the reaction mixture. Generally, temperatures of 50° to 120° C. are suitable.

Examples of suitable alcohols used in the alcoholysis are alkanols such as methanol, ethanol or propanol, and aralkanols such as benzyl alcohol.

The alcoholysis can be carried out at a temperature of usually from 0° C. to the reflux temperature of the reaction mixture, preferably from room temperature to 100° C. The alcohol can be used in an amount of generally at least 5 moles, preferably 10 to 100 moles, per mole of the compound of formula (IV).

The alcoholysis can be performed even in the absence of an acid catalyst. But it is generally advantageous to perform it in the presence of an acid catalyst of the type exemplified hereinabove. In this case, the suitable amount of the acid catalyst is generally 0.1 to 20 moles per mole of the compound of formula (IV).

When a compound of formula (IV) in which the group $$-\underset{Y}{\overset{\|}{\underset{|}{C}}}-$$

is a ketal group of the formula $$-\underset{R_7-O\quad O-R_8}{\overset{-C-}{\diagup\diagdown}}$$

is hydrolyzed, or is subjected to alcoholysis in the presence of water, the ketal group is converted to a carbonyl group $$(-\underset{O}{\overset{\|}{C}}-)$$

at the same time as the conversion of $Z_2$ to a carboxyl group or its salt or ester, and the intended product of formula (I) is obtained. On the other hand, when this starting compound is subjected to alcoholysis in the absence of water, a compound of the formula $$\text{(XIII)}$$

wherein $R_1$, $R_2$, $R_3$, $R_4$, $R_{104}$, $R_7$ and $R_8$ are as defined above, is usually formed. In this case, the intended product of formula (I) can be obtained easily by hydrolyzing the compound of formula (XIII) in the manner mentioned above.

Thus, the compound of formula (I) or its salt, ester or amide derivative can be obtained in good yields from the compound of formula (IV).

The compounds of formula (IV) are novel compounds not described heretofore in the literature, and can be prepared by the method shown in Reaction Scheme II to be given.

The substituent $R_6$ in the substituted imino group ($=NR_6$) represented by Y in formula (IV) may be the same hydrocarbon group as defined hereinabove. Preferably, it is a lower alkyl group or an aralkyl group with up to 10 carbon atoms such as benzyl or phenethyl.

The group convertible to a carboxyl group or its salt, ester or amide derivative by hydrolysis or alcoholysis may be any of those which are exemplified hereinabove with regard to the group $Z_1$ in procedure (d).

According to procedure (f) of this invention, the halogen atom ($X_1$) in the compound of the following formula $$\text{(V)}$$

wherein $R_1$, $R_2$, $R_3$, $R_4$ and $X_1$ are as defined above, can be converted to a carboxyl group or its salt, ester or amide derivative by a method known per se.

Conversion of the halogen atom to a carboxyl group or its derivative can be performed, for example, as follows:

(i) The compound of formula (V) is reacted with an alkyl or aryl alkali metal compound, especially a lower alkyl lithium (e.g., butyllithium) or an aryl lithium (e.g., phenyllitium) to replace the halogen atom ($X_1$) by the corresponding alkali metal atom, and the product is contacted with carbon dioxide gas to introduce a lithium carboxylate group (—COOLi).

(ii) The carbonyl group at the 11-position of the compound of formula (V) is temporarily protected by a ketal group $$(-\underset{R_7-O\quad O-R_8}{\overset{-C-}{\diagup\diagdown}}),$$

and the protected compound of formula (V) is reacted with metallic magnesium usually in an ether-type solvent to convert the group

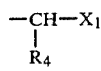

of formula (V) to the group

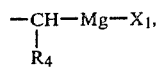

which can be converted to the group

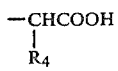

by blowing carbon dioxide gas and subsequently treating with water.

(iii) The compound of formula (V) is reacted with an alkyl or aryl alkali metal compound in the same way as described in (i) above to replace the halogen atom ($X_1$) by the corresponding alkali metal atom. The compound is then reacted with a haloformate ester such as methyl chlorocarbonate, ethyl chlorocarbonate, isopropyl chlorocarbonate, or isobutyl chlorocarbonate to convert the group $X_1$ of the compound of formula (V) to a carboxylate group (—$COOR_{104}$).

(iv) The compound of formula (V) is reacted with an alkali metal cyanide such as potassium cyanide or sodium cyanide in a water-miscible organic solvent such as methanol, ethanol, dimethyl sulfoxide or dioxane to replace the halogen atom ($X_1$) by a cyano group (—CN), and then the product is hydrolyzed or is subjected to alcoholysis in the manner mentioned above with regard to procedure (e) to convert the group $X_1$ to a carboxyl group or its salt, ester or amide derivative.

The compounds of formula (V) used as the starting material in procedure (f) are also novel compounds, and can be synthesized by the method shown in Reaction Scheme II to be given.

According to procedure (g) of this invention, a compound of formula (I) in which the group

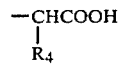

is located at the 2-position of the dibenz[b,e]azepine ring, $R_4$ is a hydrogen atom, and $R_1$, $R_2$ and $R_3$ are as defined above can be obtained by treating a compound of the formula

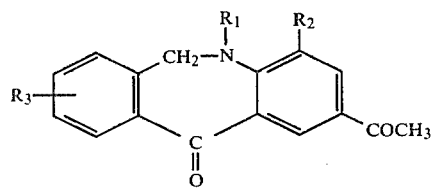

wherein $R_1$, $R_2$ and $R_3$ are as defined above, with ammonia or a primary or secondary amine in the presence of sulfur, and then hydrolyzing the treated product.

According to procedure (g), the compound of formula (V) is subjected to the Willgerodt-Kindler reaction which comprises treating it with ammonia or a primary or secondary amine in the presence of sulfur in the absence of solvent or optionally in the presence of an inert solvent such as amines (e.g., pyridine, dimethyl aniline or diethyl aniline), or ethers (e.g., dioxane, dimethylethane or diethoxyethane).

The treatment can generally be performed under heat. The heating temperature is at least about 80° C., preferably about 120° to about 200° C. Usually, the treatment is performed at atmospheric pressure, but if required, it can be performed under elevated pressure. The treatment under these conditions can be terminated in 2 to 48 hours.

The ammonia or amines that can be used in this invention are expressed by the following formula

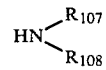

(XIV)

wherein $R_{107}$ and $R_{108}$ are as defined with regard to $R_{105}$ and $R_{106}$.

Specific examples of the compounds of formula (XIV) are ammonia, methylamine, ethylamine, isopropylamine, dibenzylamine, phenethylamine, cyclopentylamine, morpholine, and thiomorpholine. Morpholine is especially preferred.

The amount of ammonia or the amine is not critical, can be varied over a wide range. Generally, it is advantageous to use it in an amount of at least 1 mole, preferably 1.5 to 10 moles, per mole of the compound of formula (VI). When ammonia or the amine is used in a large excess, it can also act as a solvent.

The treatment is performed in the presence of sulfur. Sulfur may be elemental sulfur or polymerized sulfur (polysulfide). The amount of sulfur is not critical, but advantageously, it is used in an amount at least equivalent to the weight of the compound of formula (VI), preferably 1.5 to 3 times the weight of the compound of formula (VI).

The above treatment affords a compound of the general formula

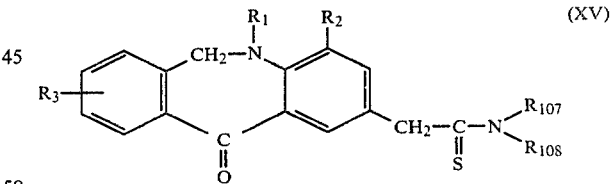

wherein $R_1$, $R_2$, $R_3$, $R_{107}$ and $R_{108}$ are as defined above, as an intermediate.

The compound of formula (XV) obtained is then hydrolyzed in a manner known per se, for example by the procedure described with regard to procedure (e).

The compounds of formula (VI) used as the starting material in procedure (g) are novel compounds not described heretofore in the literature, and can be synthesized by the method shown in Reaction Scheme IV to be given below.

According to procedure (h) of this invention, a compound of formula (I) in which the group

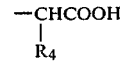

is located at the 2-position of the dibenz[b,e]azepine ring, R₄ is a hydrogen atom and R₁, R₂ and R₃ are as defined can be obtained by reacting a compound of the formula

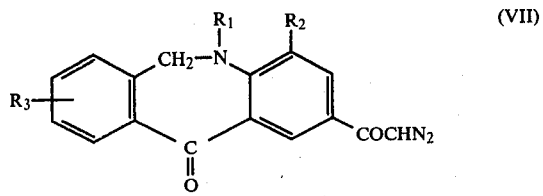

wherein $R_1$, $R_2$ and $R_3$ are as defined above, with water or an alcohol.

The reaction of the compound of formula (VII) with water or an alcohol can be performed in the presence or absence of a water-miscible organic solvent of the type described hereinabove with regard to procedure (e).

This reaction is generally performed in the presence of a metallic catalyst. Silver compounds such as silver oxide and silver acetate are especially suitable as the metal catalyst. The amount of the metal catalyst is not critical, but usually, it is from about one-tenth the weight of the compound of formula (VII) to an amount equal to the weight of this compound.

The reaction temperature is neither critical, but generally it is from room temperature to the reflux temperature of the reaction mixture. Usually, the reaction is suitably carried out at the reflux temperature.

Alternatively, when such a metal catalyst as stated above is not used, the compound of formula (VII) may be reacted with water or an alcohol at a high temperature and pressure in an autoclave. Or the compound of formula (VII) may be reacted with water or an alcohol by exposing a mixture of these to actinic light (for example, ultraviolet rays).

The alcohol that can be used in the aforesaid method depends upon the ester residue required of the ester of the compound of formula (I). Accordingly, when the compound of formula (I-c) is required, suitable alcohols can be expressed by the following formula $$R_{104}-OH \quad (XVI)$$

wherein $R_{104}$ is as defined above.

The compounds of formula (VII) used as the starting material in this procedure (h) are also novel compounds, and can be synthesized by the method shown in Reaction Scheme V.

If required, the compound of formula (I) in the form of a free acid prepared by any of the procedures (a) to (h) described above can be converted to its salt, ester or amide derivative. Conversion of the compound of formula (I) in the form of free acid to its salt, ester or amide derivative can be performed by known method, for example by treating it in a customary manner with an organic or inorganic base, an alcohol or an amine in the absence of a solvent or in the presence of a suitable solvent.

The compound of formula (I) in the form of a salt or ester can, if required, be converted to the corresponding amide derivative of the compound of formula (I) by treating it with an amine, etc. in a manner known per se.

The compound of formula (I) in the form of a salt, ester or amide derivative can, if desired, be converted to the corresponding free acid of formula (I) in a manner known per se, for example by hydrolysis or saponification.

The compounds of formula (IV) and (V) used as starting materials in procedure (e) and (f) [in the following Reaction Scheme II, the formulae (IV) and (V) are referred to inclusively as formula (B)] are novel compounds not described heretofore in the literature, and can be produced, for example, through the route shown in Reaction Scheme II.

Reaction Scheme II

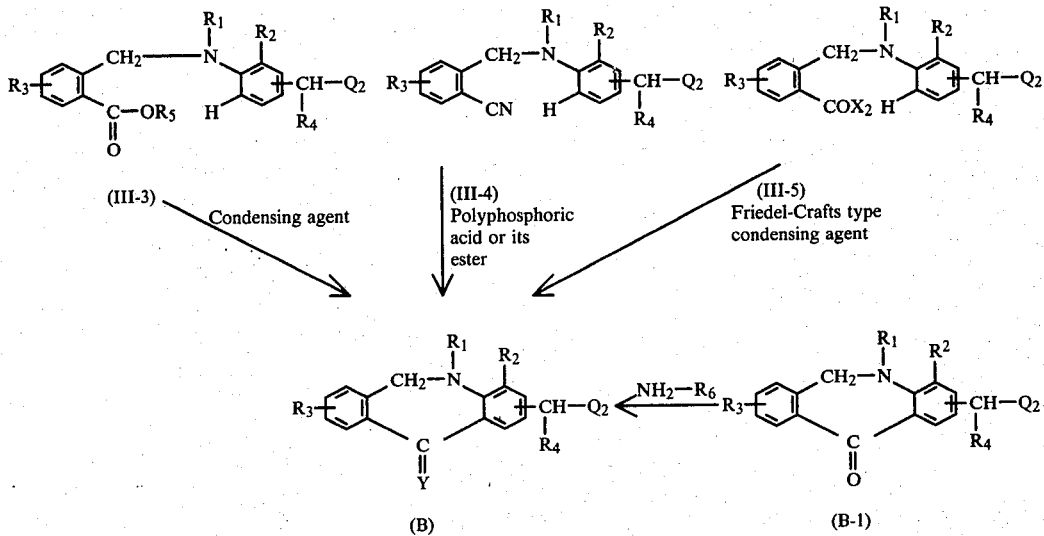

In the formulae given in Reaction Scheme II, $X_2$ represents a halogen atom, especially a chlorine atom; Y represents an oxygen atom, the group $=NR_6$, or the group

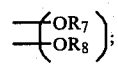

$Q_2$ has the same meaning as $Z_1$, $Z_2$ or $X_1$; and $R_1$, $R_2$, $R_3$, $R_4$, $R_5$, $R_6$, $R_7$ and $R_8$ are as defined above; with the proviso that when Y is an oxygen atom, $Q_2$ does not represent a carboxyl group or its salt, ester or amide derivative.

Cyclization of the compound of formula (III-3) to the compound of formula (B) can be performed in quite the same way as in procedure (a). Polyphosphoric acid or its esters, conc. sulfuric acid, and Friedel-Crafts type condensing agents exemplified hereinabove can be used as condensing agents in this reaction. Cyclization of the compound of formula (III-3) affords a compound of formula (B) in which Y is an oxygen atom [i.e., the compound of formula (B-1)].

Cyclization of the compound of formula (III-4) to the compound of formula (B) can be carried out in quite the same manner as described with regard to procedure (d). At the stage of treatment with polyphosphoric acid or its ester during this procedure, a compound of formula (B) in which Y is =NH is formed. This compound is extremely unstable, and is generally difficult to isolate. It should therefore be used desirably in the form of the reaction mixture as a starting material in procedure (e). Subsequent treatment of the resulting compound with water affords the compound of formula (B) in which Y is an oxygen atom.

Treatment of the compound of formula (III-5) with a Friedel-Crafts type condensing agent can give the compound of formula (B). According to this treatment, the compound of formula (III-5) can be cyclized in the presence of a Friedel-Crafts type condensing agent in an inert organic solvent such as carbon disulfide, nitrobenzene, acetonitrile, acetone or methyl ethyl ketone. Useful Friedel-Crafts condensing agents are those exemplified hereinabove. The amount of the condensing agent is not critical, but is advantageously at least 1 equivalent, preferably 2 to 20 equivalents, per mole of the compound of formula (III-5).

Advantageously, the reaction temperature is from about 0° C. to the reflux temperature of the reaction mixture, preferably from room temperature to 120° C.

In this way, the compound of formula (B) in which Y represents an oxygen atom [i.e., the compound of formula (B-1)] can be obtained. Since the Friedel-Crafts type condensing agent used in this reaction sometimes reacts also with the carboxyl group or its derivative, it is preferable not to apply this reaction to a compound of formula (III-5) in which $Q_2$ represents a carboxyl group or its salt, ester or amide derivative.

The Schiff base-forming reaction of the compound of formula (B-1) with ammonia or an amine of the formula $NH_2-R_6$ can be performed in a manner known per se.

The compounds of formulae (III-1) and (III-2) used as starting materials in procedures (a) and (d) of this invention and the compounds of formulae (III-3), (III-4) and (III-5) used in Reaction Scheme II are all novel compounds which are not described heretofore in the literature. These compounds can be generically referred to as compounds of formula (III).

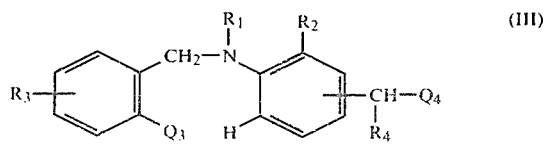

(III)

In formula (III), $Q_3$ represents the group

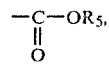

—$COX_2$ or a cyano group; $R_5$ represents a hydrogen atom, an alkali metal atom, or a monovalent hydrocarbon group; $X_2$ is a halogen atom; $Q_4$ represents a carboxyl group or its salt, ester or amide derivative, a halogen atom, or a group convertible to a carboxyl group or its salt, ester or amide derivative by hydrolysis or alcoholysis; and $R_1$, $R_2$, $R_3$ and $R_4$ are as defined above.

The compound of formula (III) can be prepared, for example, by the synthetic route shown in Reaction Scheme III.

Reaction Scheme III

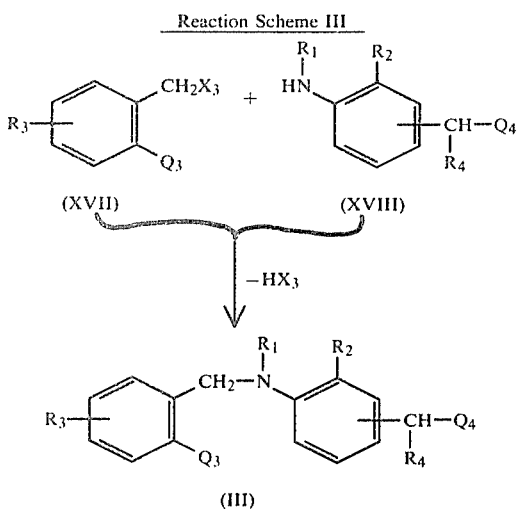

In the above formulae, $X_3$ represents a halogen atom, and $R_1$, $R_2$, $R_3$, $R_4$, $Q_3$ and $Q_4$ are as defined above.

Reaction of the compound of formula (XVII) with the compound of formula (XVIII) is generally carried out in an inert medium, for example in water, an alcohol such as methanol, ethanol or Cellosolve, a halogenated hydrocarbon such as dichloromethane, chloroform or carbon tetrachloride, an ether such as diethyl ether, tetrahydrofuran, dimethoxyethane or dioxane, a ketone such as acetone or methyl ethyl ketone, an amide such as dimethyl formamide or dimethyl acetamide, an aromatic hydrocarbon such as benzene, toluene or anisole, or a mixture of water with such an organic solvent.

The reaction is carried out usually at room temperature to the reflux temperature of the reaction mixture, preferably 30° to 100° C. It is sufficient that the reaction pressure is atmospheric pressure. If desired, however, reduced or elevated pressures may be used.

The amount of the compound of formula (XVIII) relative to the compound of formula (XVII) is not critical, but generally the suitable amount of the compound of formula (XVIII) is at least 1 mole, preferably 1.1 to 2 moles, per mole of the compound of formula (XVII).

It is frequently advantageous to perform the above reaction in the presence of an acid binder. Examples of the acid binder are metal carbonate salts such as sodium hydrogen carbonate, potassium hydrogen carbonate, sodium carbonate, potassium carbonate or lithium carbonate, alkali or alkaline earth metal hydroxides such as sodium hydroxide, potassium hydroxide, and organic bases such as triethylamine, pyridine, dimethylaniline or N-methylmorpholine. The amount of the acid binder is generally 1 to 5 equivalents per mole of the compound of formula (XVII).

The present reactions can be terminated usually in 1 to 10 hours under the conditions described above.

Thus, the compound of formula (III) can be obtained in a good yield. It can be recovered from the reaction mixture by a usual method, for example extraction, filtration, recrystallization, distillation, chromatography, sublimation, or countercurrent distribution. It may be directly used in the form of the reaction mixture as a starting material in the above process.

The compound of formula (VI) used as a starting material in procedure (g) can be easily produced, for example, by the one-step reaction shown in Reaction Scheme IV.

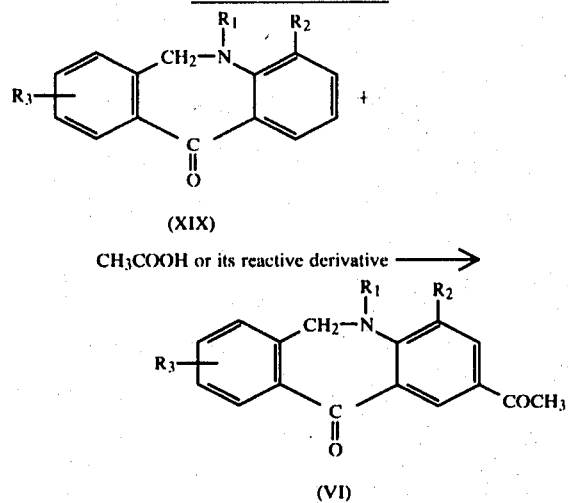

Some of the compounds of formula (XIX) are known compounds and described, for example, in J. Heterocyclic Chem., 2, 276 (1965). Even those compounds which are unknown can be prepared in the same way as in the preparation of the known compounds.

Especially suitable reactive derivatives of acetic acid to be reacted with the compound of formula (XIX) are the acid anhydrides and acid halides. These reactive derivatives can be easily obtained in a manner known per se, for example by reacting acetic acid with ketone, or in the presence of a catalyst with phosgene; or reacting acetic acid with a halogenating agent such as thionyl chloride, phosphorous oxychloride, phosphorus trichloride or phosphorus pentachloride. Thus, acetic anhydride and acetyl chloride are specific examples of the reactive derivatives of acetic acid. The use of the reactive derivative of acetic acid is advantageous in this reaction over that of free acetic acid.

The reaction of the compound of formula (XIX) with acetic acid or its reactive derivative can be performed in the absence of solvent, or preferably in the presence of a suitable inert organic solvent, for example a halogenated hydrocarbon such as methylene chloride, chloroform, carbon tetrachloride or tetrachloroethane, nitrobenzene, or carbon disulfide.

The reaction temperature is not critical, and can be varied over a wide range depending upon the type of the starting material, etc. The reaction can be performed at room temperature, but generally, it is preferred to promote the reaction by heating. The upper limit of the heating temperature differs depending upon the type of the starting material used, but it can be the decomposition temperatures of the starting material. Usually, however, temperature of up to 300° C. are preferred. Especially, temperatures in a range from 30° C. to the refluxing temperature can be used.

It is usually advantageous to continue the acylation reaction at this temperature for 0.5 to 30 hours, especially 1 to 5 hours.

The amount of acetic acid or its reactive derivative relative to the compound of formula (XIX) is not critical, and can be varied over a wide range. Generally, its amount can be at least 1 mole, preferably 1 to 10 moles, per mole of the compound of formula (XIX).

It has been found in accordance with this invention that the presence of a condensing agent of the type exemplified with regard to procedure (a) in the reaction system can markedly promote the reaction of the compound of formula (XIX) with acetic acid or its reactive derivative. Examples of suitable condensing agents are anhydrous aluminum chloride, anhydrous tin chloride, anhydrous aluminum bromide, anhydrous zinc chloride, and anhydrous titanium chloride. The amount of the condensing agent is not critical and it can be the same as that mentioned above with regard to procedure (a).

In this way, the compound of formula (VI) can be obtained in a good yield.

The compounds of formula (VII) used as starting materials in procedure (h) are novel compounds, and can be synthesized from the compounds of formula (XIX) by the method shown in Reaction Scheme V below.

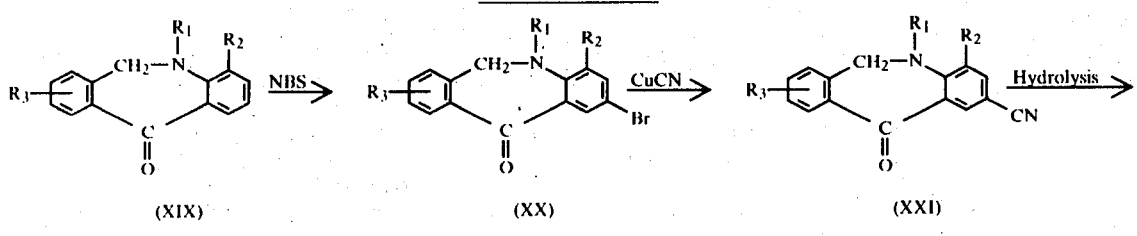

-continued

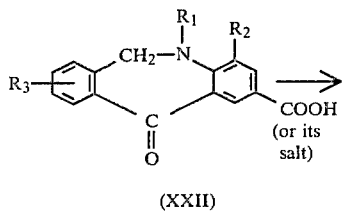 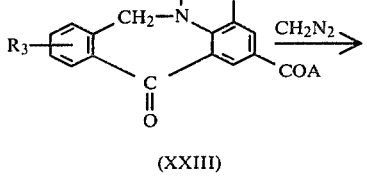 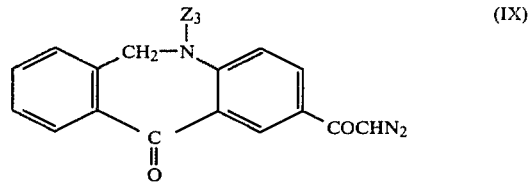

(XXII)  (XXIII)  (VII)

In the above formulae, A represents a halogen atom or the group $OCOOR_{109}$; $R_{109}$ represents a lower alkyl group; and $R_1$, $R_2$ and $R_3$ are as defined above.

Referring to Reaction Scheme V, when the compound of formula (XIX) is reacted with N-bromosuccinimide (NBS), its 2-position is selectively brominated to form the compound of formula (XX). When cuprous cyanide (CuCN) is subsequently caused to act on the compound of formula (XX), the bromine atom at the 2-position is replaced by a cyano group. Hydrolysis of the compound of formula (XXI) in a known manner affords the carboxylic acid of formula (XXII). The carboxylic acid is then treated in a customary manner; for example, it is reacted with a haloformate ester such as methyl chloroformate, ethyl chloroformate or isopropyl chloroformate, or a halogenating agent such as $POCl_3$, $PCl_3$, $PCl_5$ or $SOCl_2$ to form the active derivative of formula (XXIII). Reaction of it with diazomethane yields the compound of formula (VII).

According to still another aspect of the invention, the compound of formula (II) or its salt or ester can be prepared by a process which comprises (A) hydrolyzing or alcoholyzing a compound of the formula

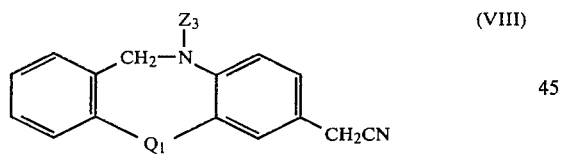

(VIII)

wherein $Z_3$ represents a hydrogen atom or an amino protecting group, and $Q_1$ represents the group

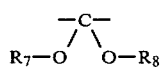

or the group

in which $R_7$ and $R_8$, independently from each other, represent a lower alkyl group, or together form a lower alkylene group, and splitting off the amino protecting group if it is present in the resulting product, or (B) reacting a compound of the formula

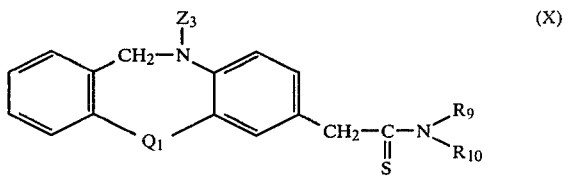

(IX)

wherein $Z_3$ is as defined above, with water or an alcohol, and splitting off the amino protecting group if it is present in the resulting product, or (C) hydrolyzing a compound of the formula

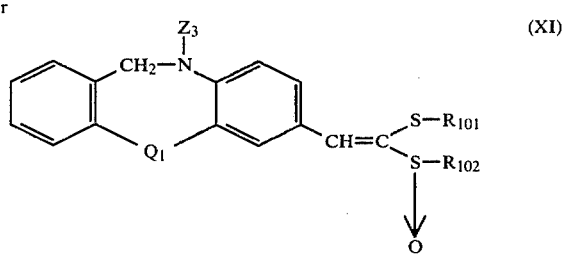

(X)

or (XI)

wherein $R_9$ and $R_{10}$, independently from each other, represent a hydrogen atom or a monovalent hydrocarbon group, or together represent a lower alkylene group optionally containing an oxygen, sulfur or nitrogen atom; $R_{101}$ and $R_{102}$, independently from each other, represent a lower alkyl group; and $Q_1$ and $Z_3$ are as defined, and splitting off the amino protecting group if it is present in the resulting product, or (D) if desired, converting the resulting free acid of formula (II) to its salt or ester, or if further desired, converting the resulting salt or ester of the compound of formula (II) to the free acid of formula (II).

In the present specification and the appended claims, the term "amino protecting group" denotes any conventional amino protecting groups which can be split off by hydrolysis or hydrogenolysis. Examples of amino protecting groups that can be split off by hydrolysis are lower alkanoyl groups and aralkyl (alkyl) oxycarbonyl groups, such as acetyl, propionyl, carbobenzyloxy or carboethoxy. Examples of amino protecting groups that can be split off by hydrogenolysis are aralkyl groups with 7 to 20 carbon atoms such as benzyl, 4-methoxybenzyl or diphenylmethyl.

Hydrolysis or alcoholysis of the compound of formula (VIII) in procedure (A) in accordance with this invention can be performed in quite the same way as described hereinabove with regard to procedure (e). As a result of the hydrolysis, the compound of formula (II) or its aminoprotected derivative is obtained in a good yield in the form of a free acid or salt. The alcoholysis affords the compound of formula (II) or its aminoprotected derivative in the form of an ester in a good yield.

After the reaction, the desired product can be recovered from the reaction mixture in a manner known per se. For example, the reaction mixture is poured into a large quantity of cold water or ice, and the precipitated compound is collected by filtration or extraction with an organic solvent. If desired, the recovered product can be purified by recrystallization, chromatography, etc.

The ketal group

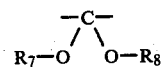

represented by $Q_1$ in the compound of formula (VIII) can be easily converted to a carbonyl group by hydrolysis, for example, and may be said to be a carbonyl protecting group. $R_7$ and $R_8$, independently from each other, represent a lower alkyl group such as methyl, ethyl or propyl, or together represent an alkylene group, especially a lower alkylene group such as an ethylene or propylene group.

The compounds of formula (VIII) used as starting materials in procedure (A) are novel compounds not described heretofore in the literature, and can be prepared, for example, from known 5,6-dihydro-2-halo-6,11-dioxodibenz[b,e]azepines of formula (1) below described in Journal of Pharmacy and Pharmacology, Vol. 21, 520 (1969) through the synthetic route shown in Reaction Scheme VI.

Reaction Scheme VI

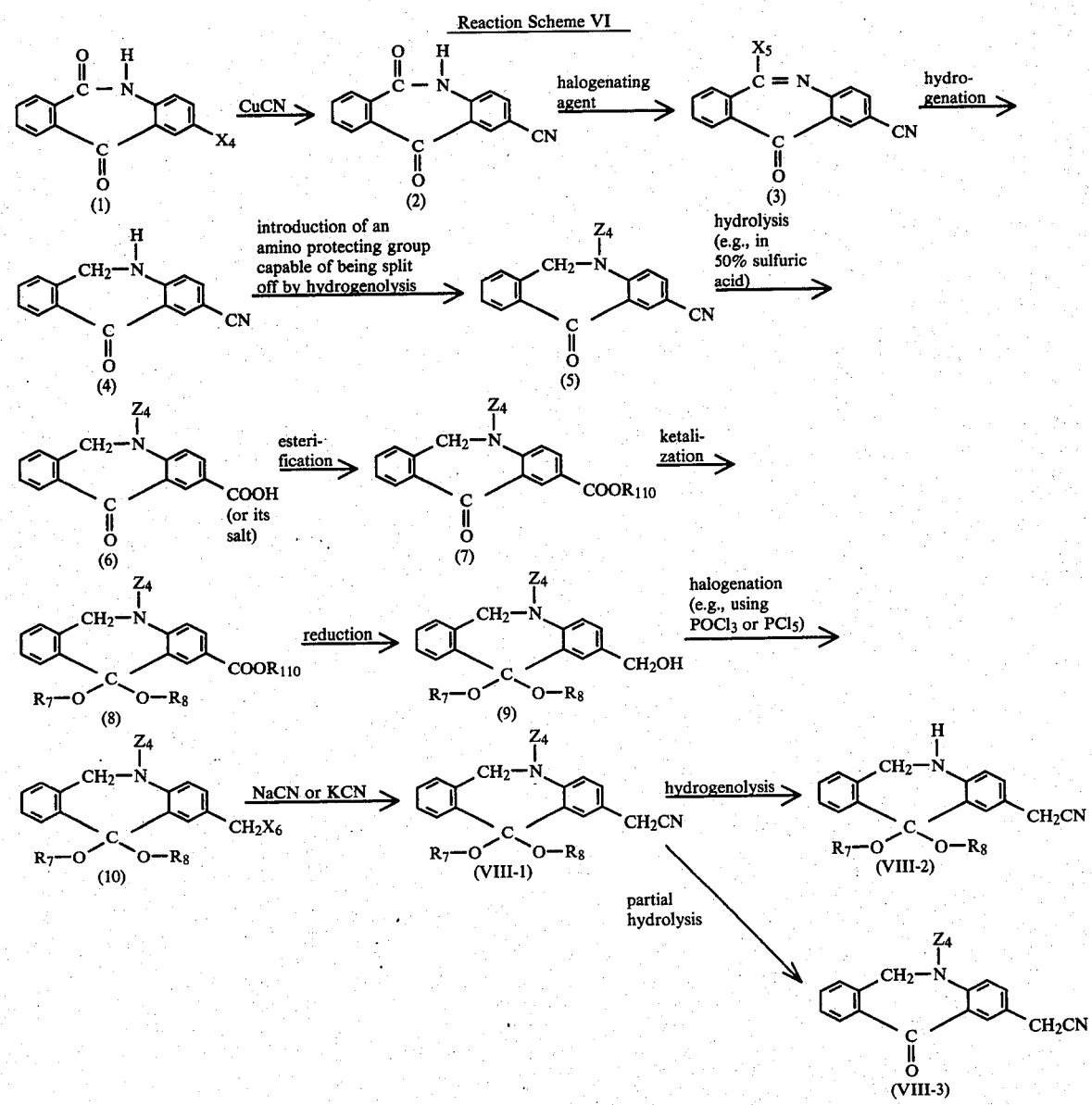

In the above formulae, $X_4$, $X_5$ and $X_6$ each represent a halogen atom; $Z_4$ represents an amino protecting group capable of being split off by hydrogenolysis; $R_{110}$ represents an ester residue; and $R_7$ and $R_8$ are as defined above.

In Reaction Scheme VI, the compound of formula (1) is reacted with cuprous cyanide to form the compound of formula (2) which is then treated with a halogenating agent such as phosphorus oxychloride, phosphorus pentachloride, phosphorus oxybromide or phosphorus pentabromide to afford the iminohalide of formula (3). The compound of formula (4) is obtained by contacting the iminohalide with hydrogen gas at atmospheric pressure or elevated pressure at room temperature to a slightly elevated temperature in the presence of a hydrogenation catalyst such as Pd-C, Pd-BaSO$_4$, Raney nickel, or Urushibara nickel.

An amino protecting group capable of being split off by hydrogenolysis, such as benzyl, 4-methoxybenzyl or diphenylmethyl, is introduced into the compound of formula (4) in a manner known per se to form the compound of formula (5) which is then hydrolyzed (for example, using 50% sulfuric acid) to convert the cyano group into a carboxyl group or its salt to form the acid of formula (6). This acid can be converted to an ordinary ester [formula (7)] in a manner known per se.

Furthermore, the ester of formula (7) is heated under reflux together with an alcohol in the presence of an acid catalyst, for example, to form the ketal compound of formula (8). The ketal compound of formula (8) is then reduced with a complex metal hydride such as LiAlH$_4$, or LiAlH$_2$(OC$_2$H$_5$)$_2$ to form the alcohol of formula (9). The alcohol is then halogenated using, for example, phosphorus trichloride or phosphorus pentachloride to form the halide of formula (10) which is then reacted with sodium cyanide or potassium cyanide to form the starting compound of formula (VIII-1).

If desired, the compound of formula (VIII-1) is hydrogenolyzed to form the starting compound of formula (VIII-2) having the amino protecting group split off. Or partial hydrolysis of the compound of formula (VIII-1) with a dilute mineral acid such as 10% hydrochloric acid gives the starting compound of formula (VIII-3).

According to procedure (B) in accordance with this invention, a compound of the following formula

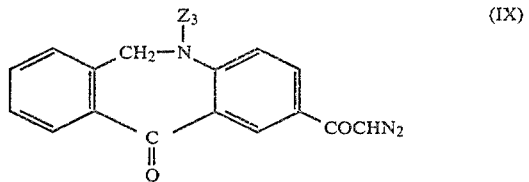

wherein $Z_3$ is as defined above, is reacted with water or an alcohol to form the corresponding free acid of formula (II) or its ester, or an amino-protected derivative of such a compound, in a good yield.

Reaction of the compound of formula (IX) with water or an alcohol can be performed in quite the same way as described above with regard to procedure (h).

The compounds of formula (IX) are also novel compounds not described heretofore in the literature, and can be prepared, for example, by reacting the compound of formula (6) obtained as an intermediate in the synthetic route shown in Reaction Scheme VI with a haloformate ester (e.g., methyl chloroformate, ethyl chloroformate, or isopropyl chloroformate) or a halogenating agent (e.g., thionyl chloride, phosphorus oxychloride, phosphorus trichloride, or phosphorus pentachloride) to convert the compound of formula (6) to a mixed acid anhydride or an acid halide, and then reacting it with a diazomethane at room temperature or a lower temperature.

According to procedure (C) of this invention, the compound of formula (II) or its salt can be prepared by hydrolyzing a compound of the formula

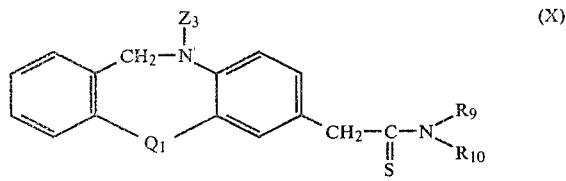

or

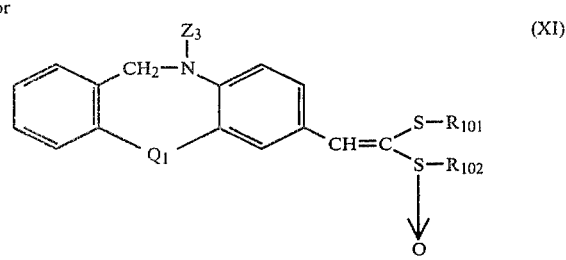

wherein $Q_1$, $Z_3$, $R_9$, $R_{10}$, $R_{101}$ or $R_{102}$ are as defined above.

Hydrolysis of the compound of formula (X) can be performed by using an aqueous solution of an alkali or an aqueous solution of an acid. Hydrolysis of the compound of formula (XI) is advantageously carried out by using an aqueous solution of an acid. These hydrolysis reactions can be performed under the same reaction conditions as described with respect to the procedure (e).

Thus, the compound of formula (II) or its salt or an amino-protected derivative of such a compound can be obtained in a good yield.

In the compound of formula (X) used as a starting material in procedure (C), the "monovalent hydrocarbon group optionally having a substituent" represented by $R_9$ and $R_{10}$ may be the same as those exemplified hereinabove with regard to formula (I-c). Specific examples of the group $$N\diagdown_{R_{10}}^{R_9}$$

which is a lower alkylene group optionally containing an oxygen, sulfur or nitrogen atom represented by $R_9$ and $R_{10}$ together are 5- or 6-membered heterocyclic groups such as pyrrolidino, piperidino, morpholino, 4-methylpiperazino and thiomorpholino.

The compounds of formula (X) are novel compounds not described heretofore in the literature, and can be prepared from 5,6-dihydro-11-oxodibenz[b,e]azepine of formula (11) [J. Heterocyclic Chem., 2, 276 (1956)] through the synthetic route shown in Reaction Scheme VII below.

Reaction Scheme VII

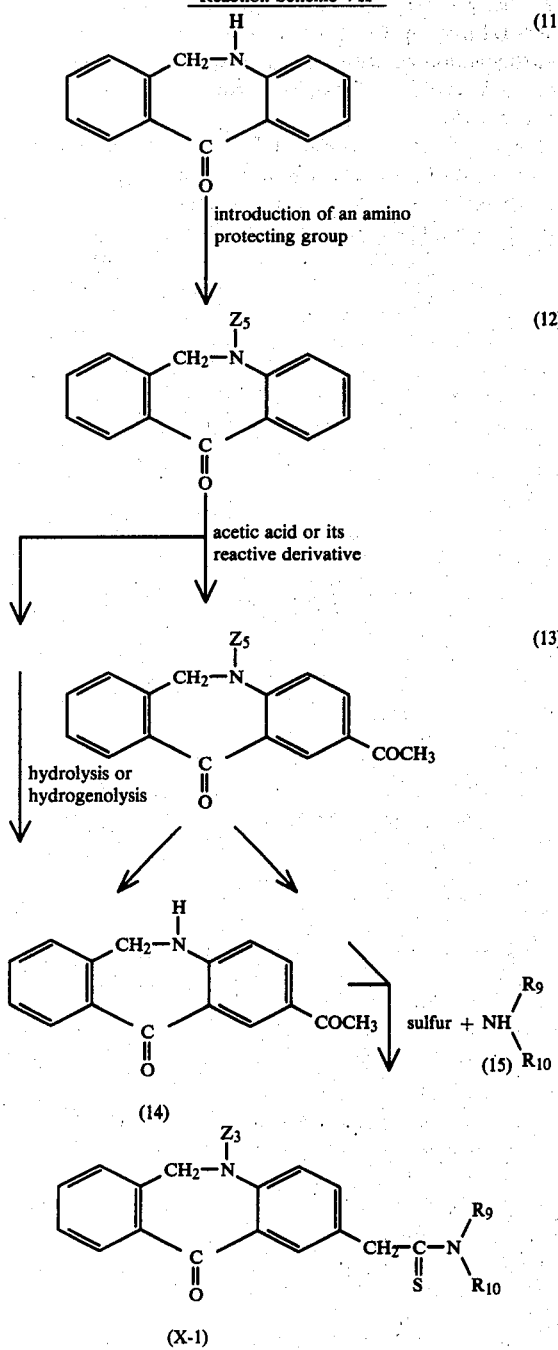

In the above formula, $Z_5$ represents an amino protecting group, and $Z_3$, $R_9$ and $R_{10}$ are as defined above.

Introduction of an amino protecting group into the compound of formula (11) in Reaction Scheme VII can be performed in a manner known per se. For example, by reacting the compound of formula (ii) with an aralkyl halide such as benzyl chloride or diphenylmethyl bromide or an acyl halide such as acetyl chloride or carbobenzoxy chloride, the compound of formula (12) can be obtained.

Conversion of the compound of formula (12) to the compound of formula (13) can be performed in quite the same way as described above with regard to Reaction Scheme IV. Conversion of the compound of formula (13) to the compound of formula (X-1) can be performed in quite the same way as described above with regard to procedure (g).

It has been found unexpectedly that in the method shown in Reaction Scheme VII, when the compound of formula (12) is reacted by using a Friedel-Crafts condensing agent, especially a complex-forming metal halide such as aluminum chloride in an amount of at least 3 times the equivalent of the compound of formula (12), an acetyl group ($CH_3CO-$) is introduced into the 2-position of the dibenz[b,e]azepine ring and simultaneously the compound of formula (14) having the amino protecting group $Z_5$ split off can be formed.

It has also been found that when the compound of formula (13) obtained in Reaction Scheme VII is heated in a solvent of the type exemplified hereinabove together with the Friedel-Crafts type condensing agent, above all a complex-forming metal halide such as aluminum chloride, the compound of formula (14) is formed in a good yield.

The amount of the metal halide used is not critical, but generally, it is used preferably in an amount of 1 to 5 equivalents per mole of the compound of formula (13). The heating temperature is at least 20° C., preferably from 30° C. to the refluxing temperature of the reaction mixture. Under these conditions, the reaction can be terminated in 0.5 to 5 hours.

Of course, the compound of formula (13) can be hydrolyzed or hydrogenolyzed in a manner known per se into the compound of formula (14). Then, by reacting the compound of formula (14) with an amine (including ammonia) of formula (15) in the presence of sulfur in accordance with the Willgerodt-Kindler reaction as described above with regard to procedure (g), a compound of formula (X-1) in which $Z_3$ is hydrogen is obtained.

The resulting compound (X-1) can be used in procedure (C) either directly or after splitting off any amino protecting group that may be present.

The compounds of formula (XI) are also novel compounds not described in the literature, and can be synthesized from the compounds of formula (6) formed as intermediates in the synthetic route shown in Reaction Scheme VI, through the synthetic route shown in Reaction Scheme VIII.

Reaction Scheme VIII

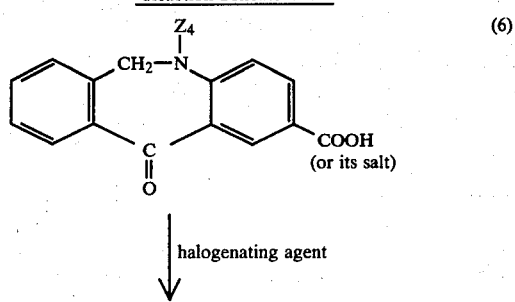

-continued
Reaction Scheme VIII

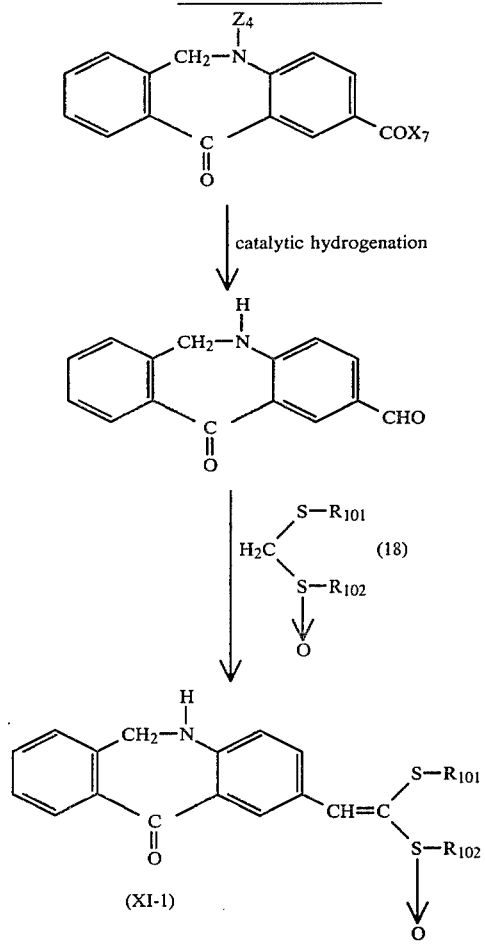

In the above formulae, $X_7$ represents a halogen atom, and $Z_4$, $R_{101}$ and $R_{102}$ are as defined above.

Referring to Reaction Scheme VIII, the compound of formula (6) is reacted in a manner known per se with a halogenating agent such as thionyl chloride, phosphorus oxychloride, phosphorus trichloride, orphosphorus pentachloride to form the acid halide of formula (16) which is then contacted with hydrogen gas under atmospheric or elevated pressures in the presence of a hydrogenation catalyst such as Pd-C or Pd-BaSO$_4$ to form the aldehyde of formula (17). The aldehyde of formula (17) is then reacted with a dialkylthiomethyl sulfoxide of formula (18)(e.g., dimethylthiomethyl sulfoxide). The reaction of the aldehyde of formula (17) with the compound of formula (18) can be performed at room temperature to the reflux temperature of the reaction mixture in a suitable aprotic solvent such as tetrahydrofuran in the presence of a basic dehydrating catalyst (for example, a 40% methanol solution of trimethyl benzyl ammonium hydroxide).

According to procedures (A) to (C), the compound of formula (II) or its salt or ester is obtained sometimes in the form of amino-protected compound depending upon the starting material used. Deprotection of the amino-protected derivative can be performed in a manner known per se. For example, if the amino protecting group can be split off by hydrolysis, the compound is hydrolyzed with acids or alkalies as described in detail with regard to procedure (e). If the amino protecting group can be split off by hydrogenolysis, the compound is contacted with hydrogen gas under atmospheric or elevated pressures at room temperature or at elevated temperatures (up to about 50° C.) in the presence of a hydrogenation catalyst having a relatively weak activity, such as Pd-C, Pd-BaSO$_4$, Raney nickel or Urushibara nickel.

The compound of formula (II) in the form of free acid produced by procedures (A) to (C) can, if required, be converted to its salt or ester in a manner known per se. For example, this can be accomplished by treating the compound of formula (II) with an organic or inorganic base or an alcohol in a customary manner in the absence of solvent or in the presence of a suitable inert solvent.

On the other hand, the compound of formula (II) in the form of a salt or ester can, if desired, be converted to the corresponding free acid of formula (II) in a manner known per se, for example by hydrolysis or saponification.

The especially preferred group of compounds of the general formula

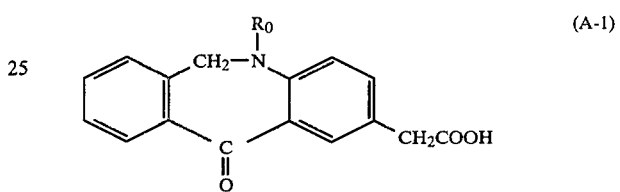

wherein $R_0$ represents a hydrogen atom or a lower alkyl group, can be very easily produced by subjecting the compound of the formula

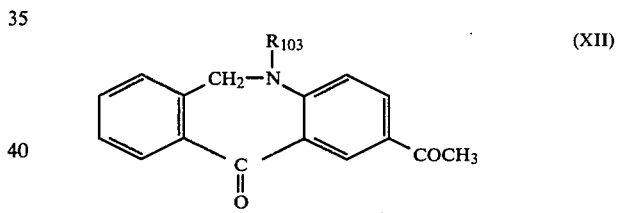

wherein $R_{103}$ represents a hydrogen atom, a lower alkyl group, or an amino protecting group capable of being split off by hydrogenolysis, which can be synthesized according to Reaction Schemes IV and VII to the Willgerodt-Kindler reaction, subsequently hydrolyzing the product, the hydrogenolyzing the product if the product contains an amino protecting group capable of being split off by hydrogenolysis. Accordingly, the compounds of formula (XII) are important key intermediate compounds of this invention, and form a part of the present invention.

Typical examples of the compounds of formula (XII) are:
5,6-dihydro-2-acetyl-11-oxodibenz[b,e]azepine,
5,6-dihydro-2-acetyl-5-methyl-11-oxodibenz[b,e]azepine,
5,6-dihydro-2-acetyl-5-ethyl-11-oxodibenz[b,e]azepine, and
5,6-dihydro-2-acetyl-5-benzyl-11-oxodibenz[b,e]azepine.

The compounds of formula (A) provided by the present invention generally have analgesic and/or anti-inflammatory activities. Among them, compounds of the following formula

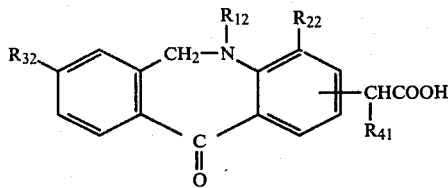

wherein $R_{12}$ represents a methyl, ethyl or n-propyl group, $R_{22}$ represents a hydrogen, chlorine or bromine atom, $R_{32}$ represents a hydrogen or chlorine atom, and $R_{41}$ represents a hydrogen atom or a methyl group, or their salts, esters or amide derivatives, and a compound of the formula

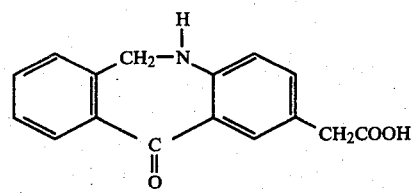

or its salts or esters have far superior analgesic and/or anti-inflammatory activities than phenylbutazone which is clinically regarded as a standard analgesic and anti-inflammatory agent. While known analgesic, anti-inflammatory agents such as aspirin, phenylbutazone or indomethacin which have been in actual use cause fairly heavy gastrointestinal lesions, it is surprising that the compounds of formula (I-b) and (II) scarcely induce gastric lesions and when administered together with indomethacin described above, can inhibit gastric ulceration caused by indomethacin.

The superior analgesic and anti-inflammatory activities of these compounds of this invention and their very slight action of inducing gastric lesions are demonstrated by animal experiments to be described.

The compounds of this invention used in the following animal experiments are shown by the following symbols.

Compounds

A:  5,6-dihydro-5-methyl-11-oxodibenz[b,e]azepine-2-acetic acid,
B:  2-(5,6-dihydro-5-methyl-11-oxodibenz[b,e]azepin-2-yl)propionic acid,
C:  5,6-dihydro-5-methyl-11-oxodibenz[b,e]azepine-1-acetic acid,
D:  5,6-dihydro-5-methyl-11-oxodibenz[b,e]azepine-3-acetic acid,
E:  5,6-dihydro-5-methyl-11-oxodibenz[b,e]azepine-2-acetic acid methyl amide,
F:  methyl 5,6-dihydro-5-methyl-11-oxodibenz[b,e]azepine-2-acetate,
G:  5,6-dihydro-4-chloro-5-methyl-11-oxodibenz[b,e]azepine-2-acetic acid,
H:  5,6-dihydro-5-methyl-8-chloro-11-oxodibenz[b,e]azepine-2-acetic acid,
I:  5,6-dihydro-5-ethyl-11-oxodibenz[b,e]azepine-2-acetic acid,
J:  5,6-dihydro-5-n-propyl-11-oxodibenz[b,e]azepine-2-acetic acid,
K:  hydroxyethyl 5,6-dihydro-5-methyl-11-oxodibenz[b,e]azepine-2-acetate,
L:  2,2-dimethyl-1,3-dioxolan-5-yl methyl 5,6-dihydro-5-methyl-11-oxodibenz[b,e]azepine-2-acetate,
M:  5,6-dihydro-11-oxodibenz[b,e]azepine-2-acetic acid.

(1) Test on analgestic activity

Male mice (ddY) with a body weight of 18 to 22 g were used in groups each consisting of 10 mice. Each of the compounds was suspended in an aqueous solution of 0.5% of carboxymethyl cellulose and 2.0% of Tween 80, and the resulting suspension was administered orally to the mice through a tube. One hour after the administration, 0.6% acetic acid was administered intraperitoneally in an amount of 0.1 ml per 10 g of body weight, and the number of writhings which occurred in the mice during a period of 20 minutes after the administration was measured. The percent inhibition on a group administered with the test compound based on the control group administered only with the vehicle was calculated from the following equation, and the $ED_{50}$ values of the test compounds were calculated from the percent inhibition in accordance with the method of Litchfield-Wilcoxon. The results are shown in Table 1.

Percent inhibition (%) = $\dfrac{\left(\begin{array}{c}\text{Average number}\\\text{of writhings in}\\\text{the control group}\\\text{administered with}\\\text{the vehicle}\end{array}\right) - \left(\begin{array}{c}\text{Average number}\\\text{of writhings in}\\\text{the group ad-}\\\text{ministered with}\\\text{the test compound}\end{array}\right)}{\left(\begin{array}{c}\text{Average number of}\\\text{writhings in the}\\\text{control group ad-}\\\text{ministered with}\\\text{the vehicle}\end{array}\right)} \times 100$

TABLE 1

| Compound | $ED_{50}$ (mg/kg, p.o.) |
| --- | --- |
| A | 9.0 (4.1–19.8) |
| B | 26.0 (12.1–55.9) |
| D | 78.0 (58.0–104.9) |
| E | 46.5 (23.3–93.0) |
| I | 15.9 (6.4–38.8) |
| J | 15.5 (4.4–54.3) |
| M | 5.1 (2.6–10.1) |
| Phenylbutazone | 130.0 (81.8–206.7) |

The parenthesized numerals show 95% confidence limits.

(2) Test on anti-inflammatory activity

Wistar male rats with a body weight of 120 to 150 g which had been fasted for 24 hours were used in groups each consisting of 5 rats. In each group, the volumes of the left hind paw were measured by a volume differential meter (made by Ugo Basile Company), and 0.1 ml of a 1% suspension of carrageenin in distilled water was subcutaneously injected into the plantar tissues of the left hind paw. One hour later, each of the test compounds was suspended in the same vehicle as used in the test on analgesic activity and administered orally to the rats. Three hours later, the volumes of the left hind paw were again measured. The increase in volume of the left hind paw of each rat in each group (the volume of edema) was measured. The percent edema inhibition on the group administered with the test compounds based on the control group administered only with the vehicle was calculated in accordance with the following equation, and the results are shown in Table 2.

$$\text{Percent inhibition (\%)} = \frac{\left(\begin{array}{c}\text{average}\\ \text{in volume in the}\\ \text{control group}\\ \text{administered with}\\ \text{the vehicle}\end{array}\right) - \left(\begin{array}{c}\text{increase in volume}\\ \text{in each rat in}\\ \text{the groups administered with the}\\ \text{test compound}\end{array}\right)}{\left(\begin{array}{c}\text{average increase in}\\ \text{volume in the control}\\ \text{group administered}\\ \text{with the vehicle}\end{array}\right)} \times 100$$

TABLE 2

| Compound | Dosage (mg/kg, p.o.) | Percent (average value ± inhibition standard error) |
|---|---|---|
| A | 10 | 28.5 ± 2.8 |
|  | 30 | 30.4 ± 4.4 |
|  | 90 | 43.9 ± 6.6 |
| B | 30 | 23.2 ± 3.2 |
|  | 90 | 38.6 ± 5.3 |
| C | 90 | 11.4 ± 12.7 |
|  | 180 | 28.6 ± 8.3 |
| D | 10 | 26.8 ± 2.9 |
|  | 30 | 36.4 ± 11.9 |
| E | 30 | 11.3 ± 4.3 |
|  | 90 | 44.8 ± 7.5 |
| F | 30 | 11.8 ± 3.4 |
|  | 90 | 27.2 ± 7/2 |
| G | 30 | 23.8 ± 6.9 |
|  | 90 | 35.4 ± 5.5 |
| H | 30 | 26.8 ± 7.3 |
|  | 90 | 34.9 ± 6.5 |
| I | 10 | 20.2 ± 6.6 |
|  | 30 | 25.6 ± 5.8 |
|  | 90 | 35.1 ± 8.2 |
| J | 30 | 18.6 ± 5.2 |
|  | 90 | 30.4 ± 4.8 |
| K | 30 | 23.5 ± 11.1 |
|  | 90 | 30.4 ± 5.5 |
| L | 30 | 17.6 ± 5.1 |
|  | 90 | 33.3 ± 4.0 |
| M | 10 | 37.3 ± 2.4 |
|  | 30 | 41.2 ± 5.4 |
| Phenyl-butazone | 30 | 20.7 ± 2.4 |
|  | 90 | 34.2 ± 5.3 |

(3) Test on the ulcerogenic activity

Each of the test compounds was orally administered in the same way as in the test on anti-inflammatory activity to Wistar male rats with a body weight of 120 to 150 g which had been fasted for 24 hours. Four hours later, they were killed with ether. Then, the stomach was removed from each rat, and the number of rats whose stomachs showed bleeding at the mucous membrane and damage beneath the mucous membrane was counted against the number of animals used. The results are shown in Table 3.

TABLE 3

| Compound | Dosage mg/kg, p.o. | Number of rats which showed a gastric ulceration/Number of rats used | |
|---|---|---|---|
|  |  | Bleeding at the mucous membrane | Damage beneath the mucous membrane |
| Vehicle alone | — | 2/32 (6.8) | 3/32 (9.4) |
| A | 30 | 2/16 (12.5) | 2/16 (12.5) |
|  | 90 | 2/16 (12.5) | 1/16 (6.3) |
|  | 270 | 1/16 (8.3) | 0/12 (0) |
| B | 30 | 1/10 (10.0) | 0/10 (0) |

TABLE 3-continued

| Compound | Dosage mg/kg, p.o. | Number of rats which showed a gastric ulceration/Number of rats used | |
|---|---|---|---|
|  |  | Bleeding at the mucous membrane | Damage beneath the mucous membrane |
| C | 90 | 1/10 (10.0) | 1/10 (10.0) |
| D | 90 | 1/15 (6.7) | 1/15 (6.7) |
| G | 30 | 1/5 (20.0) | 0/5 (0) |
| I | 90 | 0/5 (0) | 0/5 (0) |
| J | 30 | 0/5 (0) | 0/5 (0) |
| K | 90 | 0/5 (0) | 0/5 (0) |
| L | 90 | 0/5 (0) | 0/5 (0) |
|  | 30 | 2/23 (8.9) | 1/23 (4.3) |
| Phenyl-butazone | 90 | 13/34 (38.2) | 17/34 (50) |
|  | 270 | 9/19 (47.4) | 12/19 (63.2) |

(4) Toxicity test

Each of the test compounds was suspended in a physiological saline solution having dissolved therein 2% of Tween 80, and orally administered through a tube to groups of SD male and female rats (male: 130 to 150 g, female: 120 to 140 g) each group consisting of 8 rats. The rats were then observed for 2 weeks. The results and the $LD_{50}$ values calculated were as follows:

$LD_{50}$ of compound A:
  (male) 840 mg/kg
  (female) 910 mg/kg
Minimum lethal dose of compound A:
  (male) 720 mg/kg
  (female) 864 mg/kg
$LD_{50}$ of compound M:
  (male) 810 mg/kg
  (female) 840 mg/kg
Minimum lethal dose of compound M:
  (male) 720 mg/kg
  (female) 720 mg/kg
Minimum lethal dose of phenylbutazone:
  (male) 347 mg/kg
  (female) 289 mg/kg The compounds of this invention also have an inhibiting activity of platelet aggregation. It has been confirmed for example that these compounds in a concentration of $10^{-5}$ mole to $10^{-3}$ mole exhibit a dose-dependent inhibition of collagen-induced platelet aggregation in platelet-rich plasma of guinea pigs.

The compounds of this invention also have an antipyretic activity, and for example, exhibit a statistically significant antipyretic action on yeast-induced hyperthermia in doses of at least 10 mg/kg p.o.

The compounds of this invention can therefore be used as active ingredients of drugs having analgesic and/or anti-inflammatory activities or as active ingredients of drugs having an action of inhibiting platelet aggregation for the treatment and medication of man and other warm-blooded animals such as cattle, horses, swine, sheep, goats, rabbits and chickens so as to alleviate pains of various causes, reduce inflammation, inhibit thrombus formation, etc.

According to this invention, therefore, there is provided a pharmaceutical preparation having analgesic and/or anti-inflammatory activities, which comprises a therapeutically effective amount of the active compound of this invention having formula (I-b) or (II).

Any routes are available to administer the active compounds of this invention, for example oral administration, buccal administration and parenteral administration (e.g., intravenous injection, intramuscular injection, subcutaneous injection, intrarectal administration, topical administration). Oral administration is especially advantageous.

When the active compounds of this invention are used as medicines for man and animals, they are formulated into various dosage forms suitable for oral, buccal or parenteral administration according to methods known per se.

For example, the active compounds of this invention can be formulated into pharmaceutical preparations which together contain non-toxic pharmaceutically acceptable carriers or excipients normally used for pharmaceutical preparations of this kind. According to the intended uses, these pharmaceutical preparations can be made into a solid form (e.g., tablets, capsules, granules, powders, pellets, sugar-coated pills, trouches), a semisolid form (e.g., ointments, creams, suppositories), and a liquid form (e.g., injectables, emulsions, suspensions, lotions, tinctures, sprays, syrups).

Examples of the non-toxic pharmaceutically acceptable carriers or excipients include starch, gelatin, glucose, lactose, fructose, maltose, magnesium carbonate, talc, magnesium stearate, methyl cellulose, carboxymethyl cellulose or its salts, gum arabic, polyalkylene glycols, distilled water for injection, alkyl p-hydroxybenzoates, syrup, ethanol, propylene glycol, glycerol, vaseline, and Carbowax.

These drugs may also contain therapeutically useful chemicals such as dispersants, antioxidants, preservatives, stabilizers, flavoring agents, binders, lusterants, salts for changing osmotic pressures, and buffers.

The amount of the active compound of this invention in the drug can be varied widely according, for example, to the dosage form of the drug. Generally, the amount is 0.1 to 100% by weight, preferably 0.5 to 95% by weight, based on the weight of the drug. More specifically, it is desirable that the pharmaceutical preparation should contain the active compound of this invention in an amount of 1 to 100% by weight, preferably 10 to 95% by weight, when it is solid or semi-solid, and in an amount of 0.1 to 10%, preferably 0.5 to 5% by weight, when it is liquid.

The dosage of the active compound can be varied widely according to the type of the subject (whether it is man or another animal), the symptom, the physician's diagnosis, etc. Generally, it can be 1 to 30 mg/kg, preferably 2 to 20 mg/kg, per day. Higher or lower dosages can of course be used according to the symptom of a particular patient, and the physician's diagnosis. The above dosage can be administered once or a plurality of times a day.

The compounds of formula (I) provided by this invention are also useful as intermediates for the synthesis of these drugs.

The following Examples illustrate the present invention in more detail.

EXAMPLE 1

Synthesis of 5,6-dihydro-5-methyl-11-oxodibenz[b,e]azepine-2-acetic acid

A mixture of N-methyl-N-(2-carboxybenzyl)-4-carboxymethylaniline (6 g) and polyphosphoric acid (240 g) was stirred for 2 hours with heating at 120° C. The reaction mixture was poured into ice-water (500 ml) to precipitate crystals. The crystals were collected by filtration, and washed in water. Then, the crystals were vacuum-dried over diphosphorus pentoxide to obtain the desired compound (3.7 g) as yellow prismatic crystals.

m.p.: 194.1°–195.8° C. (recrystallized from acetone),
IR, $\nu_{CO}^{KBr}$: 1710 cm$^{-1}$; 1630 cm$^{-1}$,
NMR (in (CD$_3$)$_2$SO) δ: 3.22, 3H, singlet; 3.51, 2H, singlet; 4.29, 2H, singlet; 6.80–8.10, 7H, multiplet,
MAS m/e: 281.

The starting material, N-methyl-N-(2-carboxybenzyl)-4-carboxymethylaniline had been synthesized in the following manner:

A mixture of N-methyl-4-ethoxycarbonylmethylaniline (10 g), sodium hydrogencarbonate (5 g) and water (5 ml) was heated to 90° C. on an oil bath. Ethyl 2-bromomethylbenzoate (12.2 g) was gradually added dropwise to the mixture with stirring. Then, the mixture was stirred for 2 hours at 90° C. The reaction mixture was cooled, and extracted with benzene. The extract was washed with water. The benzene layer was extracted with 2 N-HCl. The aqueous layer was neutralized with potassium carbonate while cooling the layer with ice, and extracted with benzene. The benzene layer was dried over anhydrous magnesium sulfate. When the solvent was distilled off under reduced pressure, 20 g of N-methyl-N(2-ethoxycarbonylbenzyl)-4-ethoxycarbonylmethylaniline was obtained as a light-yellow oily material.

IR, $\nu_{CO}$: 1722 cm$^{-1}$
NMR (in CCl$_4$) δ: 1.19, 3H, triplet; 1.38, 3H, triplet; 3.02, 3H, singlet; 3.35, 2H, singlet; 3.80–4.55, 4H, multiplet; 4.84, 2H, singlet; 6.40–8.10, 8H, multiplet.

The oily ester (20 g) so obtained was added to a solution of sodium hydroxide (25 g) in a mixed liquor of water (300 ml) and ethanol (100 ml). The mixture was heated under reflux for 2 hours. After most of ethanol was distilled off, the mixture was washed with ether. The aqueous layer was acidified by addition of acetic acid to the layer cooled with ice, and then extracted with ether. The organic layer was dried over anhydrous magnesium sulfate, and the solvent was distilled off. The residue was recrystallized from methanol-benzene to obtain N-methyl-N-(2-carboxybenzyl)-4-carboxymethylaniline (12.2 g) as colorless prismatic crystals.

m.p.: 154.6°–156.6° C.
IR, $\nu_{CO}^{KBr}$: 1698 cm$^{-1}$
NMR (in (CD$_3$)$_2$SO) δ: 3.04, 3H, singlet; 3.38, 2H, singlet; 4.87, 2H, singlet; 6.40–8.05, 8H, multiplet.
MAS m/e: 299.

EXAMPLE 2

Synthesis of 5,6-dihydro-5-ethyl-11-oxodibenz[b,e]azepine-2-acetic acid

A mixture of N-ethyl-N-(2-carboxybenzyl)-4-carboxymethylaniline (6 g), and polyphosphoric acid (240 g) was treated in the same manner as in Example 1 to obtain the desired compound (3.5 g).

m.p.: 141.1°–144.0° C.
IR, $\nu_{CO}^{KBr}$: 1705 cm$^{-1}$; 1630 cm$^{-1}$,
NMR (in (CD$_3$)$_2$SO) δ: 1.05–1.28, 3H, triplet; 3.45–3.80, 2H, quartet; 3.49, 2H, singlet; 4.26, 2H, singlet; 6.8–7.98, 7H, multiplet,
MAS m/e: 295.

The starting N-ethyl-N(2-carboxybenzyl)-4-carboxymethylaniline had been synthesized in the following manner:

Ethyl iodide (35.1 g) was gradually added dropwise to a mixed liquid of ethyl 4-(N-benzenesulfonyl- )aminophenylacetate (60 g), potassium carbonate (39 g), and acetone (500 ml) while stirring and refluxing it. Then, the mixture was refluxed for 2 hours with stirring. The mixture was cooled, and the precipitated crystals were removed by filtration. The filtrate was distilled for removal of the solvent. The residue was dissolved in benzene, and the solution was washed in water, followed by drying over magnesium sulfate. The dried product was distilled to remove the solvent, and the residue was recrystallized from n-hexane to obtain 64.3 g (m.p. 99.8°–100.8° C.) of ethyl 4-(N-ethyl-N-benzeneslfonyl) aminophenylacetate as prismatic crystals. Subsequently, 48% hydrobromic acid (380 ml) and phenol (64.3 g) were added to the ethyl ester, and the mixture was refluxed for 4 hours. While being cooled, the refluxed mixture was washed with benzene, and distilled to remove the aqueous layer. To the residue was added benzene, and the mixture was distilled to remove moisture and crude 4-(N-ethyl)aminophenylacetic acid hydrobromide was obtained. Then, ethanol (300 ml) was added to the hydrobromide. While being cooled, the mixture was saturated with hydrogen chloride gas. With the introduction of hydrogen chloride gas, the mixture was refluxed for 4 hours. After the reaction, the solvent was distilled off. The residue was dissolved in water, and the solution was washed with ether. The aqueous layer was neutralized with potassium carbonate while cooling the layer with ice, and extracted with ether. The extract was dried over magnesium sulfate. After the solvent was distilled off, the residue was vacuum-distilled to obtain 26.8 g of the desired N-ethyl-4-ethoxycarbonylmethylaniline as a fraction boiling at 112.5° C. at 0.02 mmHg.

IR, $\nu_{NH}^{NaCl}$: 3370 cm$^{-1}$, $\nu_{CO}^{NaCl}$: 1730 cm$^{-1}$,

NMR (in CDCl$_3$) δ: 1.22, 3H+3H, triplet; 3.12, 2H, quartet; 2.9–3.6, 1H, broad; 3.47, 2H, singlet; 4.09, 2H, quartet; 6.4–7.2, 4H, multiplet.

N-ethyl-4-ethoxycarbonylmethylaniline (10.4 g) so obtained, sodium hydrogencarbonate (6.3 g), water (10 ml), and ethyl 2-bromomethylbenzoate (14.6 g) were treated in the same manner as described in Example 1 for the preparation of the starting material, thereby to obtain N-ethyl-N-(2-ethoxycarbonylbenzyl)-4-ethoxycarbonylmethylaniline (21.4 g).

IR, $\nu_{CO}^{NaCl}$: 1710 cm$^{-1}$,

NMR (in CDCL$_3$) δ: 1.1–1.34, 3H+3H, triplet; 1.27–1.51, 3H, triplet; 3.28–3.52, 2H, quartet; 3.46, 2H, singlet, 3.93–4.29, 2H, quartet; 4.18–4.54, 2H, quartet; 4.86, 2H, singlet; 6.46–8.10, 8H, multiplet.

The resulting N-ethyl-N-(2-ethoxycarbonylbenzyl)-4-ethoxycarbonylmethylaniline (21.4 g), sodium hydroxide (20 g), water (200 ml) and ethanol (100 ml) were treated in the same manner as described in Example 1 for the preparation of the starting material, thereby obtaining N-ethyl-N-(2-carboxybenzyl)-4-carboxymethylaniline (8.1 g).

m.p.: 159.7°–160.4° C.,

IR, $\nu_{CO}^{KBr}$: 1700 cm$^{-1}$,

NMR (in (CD$_3$)$_2$SO) δ: 1.04–1.26, 3H, triplet; 3.28–3.61, 2H, quartet; 3.35, 2H, singlet; 4.81, 2H, singlet; 6.3–8.1, 8H, multiplet.

EXAMPLE 3

Synthesis of 5,6-dihydro-5-n-propyl-11-oxodibenz[b,e]azepine-2-acetic acid

A mixture of N-n-propyl-N(2-carboxybenzyl)-4-car carboxymethylaniline (8 g) and polyphosphoric acid (320 g) was treated in the same manner as described in Example 1 to obtain the desired compound (3.1 g)

m.p.: 125.9°–126.3° C.,

IR, $\nu_{CO}^{KBr}$: 1705 cm$^{-1}$; 1635 cm$^{-1}$,

NMR (in (CD$_3$)$_2$SO) δ: 0.71–0.95, 3H, triplet; 1.20–1.90, 2H, multiplet; 3.30–3.70, 2H, multiplet; 3.49, 2H singlet; 4.29, 2H, singlet; 6.8–8.05, 7H, multiplet, MAS m/e: 309.

The starting material employed above was synthesized in the following manner:

N-n-propyl-4-ethoxycarbonylmethylaniline (11.1 g, b.p. 131°–135°C./0.5 mmHg), sodium hydrogencarbonate (6.3 g), water (10 ml), and ethyl 2-bromomethylbenzoate (14.6 g) were treated in the same manner as described in Example 1 to obtain N-n-propyl-N-(2-ethoxycarbonylbenzyl)-4-ethoxycarbonylmethylaniline (16.5 g).

IR, $\nu_{CO}^{NaCl}$: 1720 cm$^{-1}$,

NMR (in CDCl$_3$) δ: 0.79–2.00, 11H, multiplete; 3.21–3.51, 2H, triplet; 3.48, 2H, singlet; 3.95–4.56, 4H, multiplet; 4.90, 2H, singlet; 6.40–8.13, 8H, multiplet.

N-n-propyl-N-(2-ethoxycarbonylbenzyl)-4-ethoxycarbonylmethylaniline (16.5 g) so obtained, sodium hydroxide (20 g), water (100 ml), and ethanol (100 ml) were treated in the same manner as described in Example 1, to give N-n-propyl-N-(2-carboxybenzyl)-4-carboxymethylaniline (10.8 g).

m.p.: 162.7°–162.9° C. (prismatic crystals).

IR, $\nu_{CO}^{KBr}$: 1695 cm$^{-1}$,

NMR (in (CD$_3$)$_2$SO) δ: 0.78–1.02, 3H, triplet; 1.20–1.95, 2H, multiplet; 3.20–3.45, 2H, triplet, 3.34, 2H, singlet; 4.83, 2H, singlet; 6.40–8.02, 8H, multiplet.

EXAMPLE 4

Synthesis of 5,6-dihydro-5-methyl-11-oxodibenz[b,e]azepine-1-acetic acid and 5,6-dihydro-5-methyl-11-oxodibenz[b,e]azepine-3-acetic acid A mixture of N-methyl-N-(2-carboxybenzyl)-3-carboxymethylaniline (15 g) and polyphosphoric acid (600 g) was stirred for 2 hours with heating at 120° C. After the reaction, the reaction mixture was poured into ice-water (1.5 liters) to precipitate crystals. The crystals were collected by filtration to obtain 2.3 g of 5,6-dihydro-5-methyl-11-oxodibenz[b,e]azepine-3-acetic acid, one of the desired compounds, as yellow crystals.

m.p.: 161°–162.5° C.

IR, $\nu_{CO}^{KBr}$: 1705 cm$^{-1}$; 1615 cm$^{-1}$,

NMR (in (CD$_3$)$_2$SO) δ: 3.24, 3H, singlet; 3.60, 2H, singlet; 4.30, 2H, singlet; 6.65–8.15, 7H, multiplet, MAS m/e: 281.

The filtrate resulting from the filtration of the above reaction mixture which had been poured into ice-water was extracted twice with 1 liter of chloroform each. The chloroform layer was dried over anhydrous sodium sulfate, and distilled to remove the solvent. The residue was recrystallized from acetone to obtain 5,6-dihydro-5-methyl-11-oxodibenz[b,e]azepine-1-acetic acid (2.7 g) melting at 178.3°–180.8° C. as yellow crystals.

IR, $\nu_{CO}^{KBr}$: 1695 cm$^{-1}$; 1605 cm$^{-1}$,

NMR (in (CD$_3$)$_2$SO) δ: 3.12, 3H, singlet; 3.81, 2H, singlet; 4.26, 2H, singlet; 6.65–7.65, H, multiplet, MAS m/e: 281.

The starting material employed above had been synthesized in the same manner as described in Example 1. That is, N-methyl-3-ethoxycarbonylmethylaniline (20.7 g), sodium hydrogencarbonate (19 g), water (30 ml) and ethyl 2-bromomethylbenzoate (27.5 g) were used to produce N-methyl-N-(2-ethoxycarbonylbenzyl)-3-ethoxycarbonylmethylaniline (26 g) as a light yellow oil. Then, N-methyl-N-(2-ethoxycarbonylbenzyl)-3-ethoxycarbonylmethylaniline (26 g) so produced, sodium hydroxide (40 g), water (450 ml) and ethanol (150 ml) were used to prepare N-methyl-N-(2-carboxybenzyl)-3-carboxymethylaniline (14.8 g).

m.p.: 158.6°–159.6° C.,

IR, $\nu_{CO}^{KBr}$: 1710 cm$^{-1}$, 1685 cm$^{-1}$,

NMR (in (CD$_3$)$_2$SO) δ: 3.02, 3H, singlet; 3.44, 2H, singlet; 4.88, 2H, singlet; 6.4–8.1, 8H, multiplet.

EXAMPLE 5

Synthesis of 5,6-dihydro-5-methyl-8-chloro-11-oxodibenz[b,e]azepine-2-acetic acid A mixture of N-methyl-N-(2-carboxy-5-chlorobenzyl)-4-carboxymethylaniline (2.0 g) and polyphosphoric acid (80 g) was treated in the same manner as described in Example 1 to obtain the desired compound (1.0 g) as yellow needle-like crystals.

m.p.: 191.0°–193.5° C. (decomposition point; recrystallized from chloroform-benzene), IR, $\nu_{OH}^{KBr}$: 3050–2550 cm$^{-1}$; $\nu_{CO}^{KBr}$: 1710 cm$^{-1}$; 1630 cm$^{-1}$, NMR (in (CD$_3$)$_2$SO) δ: 3.22, 3H, singlet; 3.50, 2H, singlet; 4.29, 2H, singlet; 6.92, 1H, doublet; 7.50, 4H, multiplet; 7.94, 1H, doublet.

The starting material, N-methyl-N-(2-carboxy-5-chlorobenzyl)-4-carboxymethylaniline, had been synthesized in the following manner:

N-methyl-4-ethoxycarbonylmethylaniline (5.8 g) and 2-trichloromethyl-5-chlorobenzylbromide (9.7 g) were dissolved in acetone (50 g), and anhydrous potassium carbonate (4.2 g) was added to the solution. The mixture was heated for 3 days with stirring. Then, the inorganic material was removed by filtration, and the solvent was distilled off. The residue was purified by liquid chromatography using a silica gel column to obtain N-methyl-N-(2-trichloromethyl-5-chlorobenzyl)-4-ethoxycarbonylmethylaniline (6.5 g).

IR, $\nu_{CO}^{Film}$: 1730 cm$^{-1}$,

NMR (in CDCl$_3$) δ: 1.24. 3H, triplet; 3.06, 3H, singlet; 3.50, 2H, singlet; 4.15; 2H, quartet; 5.00, 2H, singlet; 6.68, 2H, doublet; 7.12, 2H, doublet; 7.40, 1H, doublet-doublet; 7.49, 1H, doublet; 8.02, 1H, doublet.

N-methyl-N-(2-trichloromethyl-5-chlorobenzyl)-4-ethoxycarbonylmethylaniline (5.0 g) so obtained was dissolved in ethanol (30 g) and water (15 g), and sodium hydroxide (6.0 g) was added. The mixture was refluxed for 5 hours with heating. The reaction mixture was concentrated, and the concentrate was acidified with dilute acetic acid. The precipitated crystals were collected by filtration. The crystals were recrystallized from acetone benzene to obtain the desired N-methyl-N(2-carboxy-5-chlorobenzyl)-4-carboxymethylaniline (2.3 g) as light-yellow scaly crystals.

m.p.: 168°–171° C.,

IR, $\nu_{OH}^{KBr}$: 3020–2520 cm$^{-1}$; $\nu_{CO}^{KBr}$: 1695 cm$^{-1}$,

NMR (in (CD$_3$)$_2$SO) δ: 2.02, 3H, singlet; 4.74, 2H, singlet; 6.56, 2H, doublet; 7.00, 2H, doublet; 7.10, 1H, doublet; 7.38, 1H, doublet-doublet; 7.93; 1H, doublet.

EXAMPLE 6

Synthesis of ethyl 5,6-dihydro-5-methyl-11-oxodibenz[b,e]azepine-2-acetate

A mixture of N-methyl-N-(2-cyanobenzyl)-4-ethoxycarbonylmethylaniline (6 g) and polyphosphoric acid (60 g) was stirred for 2 hours with heating at 130°–140° C. After the reaction, the reaction mixture was poured into iced water (500 ml) to precipitate crystals. The crystals were collected, washed in water, and then vacuum-dried over diphosphorus pentoxide to obtain the desired compound (2.5 g) as yellow prismatic crystals.

IR, $\nu_{CO}^{KBr}$: 1725 cm$^{-1}$; 1635 cm$^{-1}$,

NMR (in (CD$_3$)$_2$SO) δ: 1.05, 3H, triplet; 3.22, 3H, singlet, 3.51, 2H, singlet; 3.49, 2H, quartet; 4.29, 2H, singlet; 6.80–8.10, 7H, multiplet.

The starting N-methyl-N-(21 -cyanobenzyl)-4-ethoxycarbonylmethylaniline had been synthesized in the following manner:

N-Methyl-4-ethoxycarbonylmethylaniline (10 g), sodium hydrogencarbonate (5 g), water (5 ml), and 2-bromomethylcyanobenzene (12.2 g) were treated in the same manner as described in Example 1 for the preparation of the starting material. 18 g of N-methyl-N-(2-cyanobenzyl)-4-ethoxycarbonylmethylaniline was obtained as a light-yellow oily material.

IR, $\nu_{CN}^{KBr}$: 2240 cm$^{-1}$; $\nu_{CO}^{KBr}$: 1730 cm$^{-1}$,

NMR (in CDCl$_{3l}$) δ: 1.23, 3H, triplet; 3.05, 3H, singlet; 3.50, 2H, singlet; 4.13, 2H, quartet; 4.69, 2H, singlet; 6.55–7.80, 8H, multiplet.

EXAMPLE 7

Synthesis of 5,6-dihydro-4-nitro-5-methyl-11-oxodibenz[b,e]azepine-2-acetic acid A solution of 1.20 1 g of 5,6-dihydro-5-methyl-11-oxodibenz[b,e]azepine-2-acetic acid in 20 ml of acetic acid-conc. sulfuric acid (1:1) was cooled to 0° C. While stirring the solution, a mixture at 0°–1° C. of niter (2.4 g) and conc. sulfuric acid (6 ml) was added dropwise over the course of 10 minutes. Then, the mixture was poured over ice to precipitate crystals. The crystals were collected by filtration, and recrystallized from acetonecyclohexane. Thereby was obtained 0.55 g of 5,6-dihydro-4-nitro-5-methyl-11-oxodibenz[b,e]azepine-2-acetic acid (prismatic crystals) having a melting point of 184°–186° C.

IR, $\nu_{OH}^{KBr}$: 2800–2350 cm$^{-1}$; $\nu_{CO}^{KBr}$: 1700 cm$^{-1}$; 1650 cm$^{-1}$; $\nu_{NO_2}^{KBr}$: 1505 cm$^{-1}$, 1275 cm$^{-1}$,

NMR (in CDCl$_3$) δ: 2.82, 3H, singlet; 3.68, 2H, singlet; 4.38, 2H, singlet; 7.10–8.40, 6H, multiplet, MAS m/e: 326.

EXAMPLE 8

Synthesis of 5,6-dihydro-4-bromo-5-methyl-11-oxodibenz[b,e]azepine-2-acetic acid Methyl 5,6-dihydro-5-methyl-11-oxodibenz[b,e]azepine-2-acetate (0.750 g) was dissolved in chloroform (10 ml), and N-bromosuccinimide (0.550 g) was added to the solution. The mixture was refluxed overnight, and cooled. The mixture was then washed with water and dried over anhydrous magnesium sulfate. The solvent was distilled off under reduced pressure to give an oily material. A 10% sodium carbonate aqueous solution (15 ml) and ethanol (10 ml) were added to the oily material, and the mixture was refluxed overnight. The contents were concentrated to ⅓ the original volume under reduced pressure with heating. The concentrate was treated with activated carbon powder, and acidified with 10% HCl with ice cooling. The precipitated crystals were collected by filtration and recrystallized from acetone to afford 5,6-dihydro-4-bromo-5-methyl-11-oxodibenz[b,e]azepine-2-acetic acid (prismatic crystals, 0.100 g) having a melting point of 164°–167° C.

IR, $\nu_{OH}^{KBr}$: 2800–2350 cm$^{-1}$; $\nu_{CO}^{KBr}$: 1695 cm$^-$; 1635 cm$^{-1}$,

NMR (in CDCl$_3$) δ: 2.80, 3H, singlet; 3.65, 2H, singlet; 4.40, 2H, singlet; 7.20–8.30, 6H, multiplet, MAS m/e: 359.

EXAMPLE 9

Synthesis of 5,6-dihydro-4-chloro-5-methyl-11-oxodibenz[b,e]azepine-2-acetic acid Methyl 5,6-dihydro-5-methyl-11-oxodibenz[b,e]azepine-2-acetate (2.0 g) was dissolved in chloroform (50 ml), and the solution was refluxed for 2 hours with the addition of N-chlorosuccinimide (1.4 g). The reaction mixture was treated in the same manner as described in Example 8 to obtain 5,6-dihydro-4-chloro-5-methyl-11-oxodibenz[b,e]azepine-2-acetic acid (1.2 g) having a melting point of 168.0°–170° C. (prismatic crystals).

IR, $\nu_{CO}^{KBr}$: 1700 cm$^{-1}$, 1640 cm$^1$,

NMR (in CDCl$_3$) δ: 2.80, 3H, singlet; 3.65, 2H, singlet; 4.40, 2H, singlet; 7.10–8.20, multiplet, MAS m/e: 315.

EXAMPLE 10

Synthesis of methyl 5,6-dihydro-5-methyl-11-oxodibenz[b,e]azepine-3-acetate 5,6-Dihydro-5-methyl-11-oxodibenz[b,e]azepine-3-acetic acid was esterified with methanol-sulfuric acid in a customary manner to afford methyl 5,6-dihydro-5-methyl-11-oxodibenz[b,e]azepine-3-acetate having a melting point of 88.4°–90.5° C.

IR, $\nu_{CO}^{KBr}$: 1725 cm$^{-1}$; 1630 cm$^{-1}$,

NMR (in CDCl$_3$) δ: 3.11, 2H, singlet; 3.26, 3H, singlet; 3.70, 3H, singlet; 4.27, 2H, singlet; 6.70–8.40, 7H, multiplet, MAS m/e: 295.

EXAMPLE 11

Synthesis of methyl 5,6-dihydro-5-methyl-11-oxodibenz[b,e]azepine-2-acetate

In the same manner as described in Example 10, 1.9 g of methyl 5,6-dihydro-5-methyl-11-oxodibenz[b,e]azepine-2-acetate was obtained as yellow prismatic crystals from 2 g of 5,6-dihydro-5-methyl-11-oxodibenz[b,e]azepine-2-acetic acid.

m.p.: 134.5°–135.6° C.,

IR, $\nu_{CO}^{KBr}$: 1720 cm$^{-1}$; 1628 cm$^{-1}$,

NMR (CDCl$_3$) δ: 3.24, 3H, singlet; 3.61, 2H, singlet; 3.69, 3H, singlet; 4.25. 2H, singlet; 6.75–8.30, 7H, multiplet, MAS m/e: 295.

EXAMPLE 12

Synthesis of 5,6-dihydro-5-methyl-11-oxodibenz[b,e]azepine-2-acetic acid hydroxyethyl ester 5,6-Dihydro-5-methyl-11oxodibenz[b,e]azepine-2-acetic acid (2g), ethylene glycol (150 ml), and p-toluene-sulfonic acid (0.05 g) were put into an esterification apparatus, and refluxed for 3 hours. After the reaction, excess ethylene glycol was distilled off under reduced pressure, and the residue was dissolved in chloroform. The solution was washed with a 5% aqueous solution of potassium carbonate, washed in water, and dried over MgSO$_4$. Then, the solvent was distilled off to give 2.1 g of an oily material. The oily material was purified by column chromatography over 50 g of Wakogel C-200 and elution of the column with chloroform gave 1.3 g of an oily matter.

IR, $\nu_{OH}^{KBr}$: 3440 cm$^{-1}$, $\nu_{CO}^{KBr}$: 1735 cm$^{-1}$; 1635 cm$^{-1}$,

NMR (in CDCl$_3$) δ: 1.8–2.3, 1H, broad; 3.23, 3H, singlet; 3.50–3.80, 4H, multiplet; 4.10–4.40, 4H, multiplet; 6.70–8.20, 7H, multiplet.

EXAMPLE 13

Synthesis of 5,6-dihydro-5-methyl-11-oxodibenz[b,e]azepine-2-acetic acid 2,2-dimethyl-1,3-dioxolan-5-ylmethyl ester Methyl 5,6-dihydro-5-methyl-11-oxodibenz[b,e]azepine-2-acetate (1.5 g) was dissolved in Solketal (20 ml), and 50% oily sodium hydride (0.2 g) was added. The mixture was maintained at 80°–100° C. under reduced pressure using an aspirator. The reaction mixture was poured into water (150 ml) and acetic acid (0.5 ml), and the system was extracted with dichloromethane. The extract was dried over MgSO$_4$, and then, the solvent was distilled off. The residual oily matter was subjected to liquid column chromatography using 100 g of Wakogel C-200 to afford the desired compound as a yellow oily material (0.950 g) eluted with a mixed liquid of benzene-dichloromethane (1:1).

IR, $\nu_{CO}^{KBr}$: 1730 cm$^{-1}$; 1630 cm$^-$,

NMR (in CDCl$_3$) δ: 1.35, 3H, singlet; 1.40, 3H, singlet; 3.22, 3H, singlet; 3.61, 2H, singlet; 3.6, 1H, multiplet; 4.10, 4H, multiplet; 4.22, 2H, singlet; 6.83, 1H, doublet; 7.30, 4H, multiplet; 7.70, 1H, multiplet; 8.13, 1H, doublet.

EXAMPLE 14

Synthesis of methyl 5,6-dihydro-5-ethyl-11-oxodibenz[b,e]azepine-2-acetate 5,6-Dihydro-5-ethyl-11-xodibenz[b,e]azepine-2-acetic acid was treated in the same manner as described in Example 10 to afford methyl 5,6-dihydro-5-ethyl-11-oxodibenz[b,e]azepine-2-acetate.

m.p.: 115.7°–119.2° C.,

IR, $\nu_{CO}^{KBr}$: 1740 cm$^{-1}$; 1635 cm$^{-1}$,

NMR (in CDCl$_3$) δ: 1.13–1.37, 3H, triplet; 3.42–3.78, 2H, quartet; 3.58, 2H, singlet; 3.68, 3H, singlet; 4.22, 2H, singlet; 6.79–8.20, 7H, multiplet.

EXAMPLE 15

Synthesis of methyl 5,6-dihydro-5-n-propyl-11-oxodibenz[b,e]azepine-2-acetate In the same manner as described in Example 10, methyl 5,6-dihydro-5-n-propyl-11-oxodibenz[b,e]azepine-2-acetate was obtained as a yellow oily material from 5,6-dihydro-5-n-propyl-11-oxodibenz[b,e]azepine-2-acetic acid.

IR, $\nu_{CO}^{KBr}$: 1740 cm$^{-1}$; 1635 cm$^{-}$,

NMR (in CDCl$_3$) δ: 0.76–1.02, 3H, triplet; 1.40–2.00, 2H, multiplet; 3.30–3.60, 2H, triplet; 3.57, 2H, singlet; 3.68, 3H, singlet; 4.24, 2H, singlet; 6.75–8.20, 7H, multiplet.

EXAMPLE 16

Synthesis of 5,6-dihydro-5-methyl-11-oxodibenz[b,e]azepine-2-N-methylacetamide Methyl 5,6-dihydro-5-methyl-11-oxodibenz[b,e]azepine-2-acetate (0.6 g), a 40% aqueous solution of monomethylamine (12 ml), and methanol (18 ml) were placed in a sealed tube, and reacted at 80° C. for 20 hours. Then, the solvent was distilled off, and the residue was extracted with chloroform. The extract was washed in water and dried over anhydrous magnesium sulfate. Thereafter, chloroform was distilled off, and the residue was recrystallized from ethyl acetate to obtain the desired compound (0.5 g) as yellow crystals.

m.p.: 192.8°–194.4° C.,

IR, $\nu_{NH}^{KBr}$: 3280 cm$^{-1}$; $\nu_{CO}^{KBr}$: 1635 cm$^{-1}$,

NMR (in CDCl$_3$) δ: 2.75, 3H, doublet; 3.26, 3H, singlet; 3.52, 2H, singlet; 4.27, 2H, singlet; 5.2–5.8, 1H, broad; 6.7–8.5, 7H, multiplet, MAS m/e: 294.

EXAMPLE 17

Synthesis of 5,6-dihydro-5-methyl-11-oxodibenz[b,e]azepine-2-acethydroxamic acid Methyl 5,6-dihydro-5-methyl-11-oxodibenz[b,e]azepine-2-acetate (1.5 g) was dissolved in methanol (80 ml), and hydroxylamine hydrochloride (1.0 g) was added to make a homogeneous solution. Then, a 28% solution (6 g) of sodium methylate in methanol was added to the homogeneous solution, and the mixture was heated for 3 hours. Then, the reaction mixture was concentrated, and after addition of water (20 ml) and dry ice (1 g), was extracted with chloroform. The extract was dried over MgSO$_4$, and then, chloroform was distilled off. The residue was stirred with benzene to form crystals. The crystals were recrystallized from benzene-tetrahydrofuran to obtain the desired compound (0.8 g) as yellow prismatic crystals.

m.p.: 137°–141° C.,

IR, $\nu^{KBr}$: 3200 cm$^{-1}$, 3150 cm$^{-1}$, 1660 cm$^{-1}$, 1622 cm$^{-1}$,

NMR (in CD$_3$)$_2$SO)δ: 3.19, 3H, singlet; 3.22, 2H, singlet; 4.25, 2H, singlet; 6.90, 1H, doublet; 7.46, 6H, multiplet; 7.99, 1H, doublet; 10.60, 1H, singlet.

EXAMPLE 18

Synthesis of 2-(5,6-dihydro-5-methyl-11-oxodibenz[b,e]azepin-2-yl)propionic acid Methyl 5,6-Dihydro-5-methyl-11-oxodibenz[b,e]azepine-2-acetate (2 g) was reacted with diethyl carbonate (30 ml) and 50% sodium hydride (oily) (1 g) for 2 hours at room temperature, and for an additional one hour at 100° C. Then, the system was returned to room temperature, and methyl iodide (3.0 ml) was added. After the reaction mixture was stirred for 2 hours, it was poured into water, and the organic layer was extracted with ether. The extract was distilled to remove the solvent, and the residue was heated under refluxing for 3 hours together with ethanol (30 ml), water (6 ml) and sodium hydroxide (1.2 g). Then, the reaction mixture was concentrated under reduced pressure. The concentrate was dissolved in water, and the solution was acidified with dilute sulfuric acid to precipitate crystals. The precipitated crystals were collected by filtration and recrystallized from tetrahydrofuran-hexane to yield 5,6-dihydro-5-methyl-11-oxodibenz[b,e]azepine-2-methylmalonic acid (0.8 g) as light-yellow crystals. m.p. 121.5°–123.0° C. (decomposition).

The resulting 5,6-dihydro-5-methyl-11-oxodibenz[b,e]azepine-2-methylmalonic acid (1.0 g) was heated for 10 minutes on an oil bath at 200° C. and was cooled. Then, the product was recrystallized from ether-hexane to afford the desired 2-(5,6-dihydro-5-methyl-11-oxodibenz[b,e]azepin-2-yl)propionic acid (0.6 g).

m.p.: 155°–157.5° C.,

IR, $\nu_{CO}^{KBr}$: 1700 cm$^{-1}$; 1625 cm$^{-1}$,

NRR (in CDCl$_3$)δ: 3.20, 3H, singlet; 3.75, 1H, quartet; 4.20, 2H, singlet; 6.85–8.21, 7H, multiplet.

EXAMPLE 19

Synthesis of methyl 2-(5,6-dihydro-5-methyl-11-oxodibenz[b,e]azepin-2-yl)propionate In the same manner as described in Example 10, 1.0 g of methyl 2-(5,6-dihydro-5-methyl-11-oxodibenz[b,e]azepin-2-yl)propionate was obtained as a yellow oily material from 2-(5,6-dihydro-5-methyl-11-oxodibenz[b,e]azepin-2-yl)propionic acid (1.0 g).

IR, $\nu_{CO}^{KBr}$: 1730 cm$^{-1}$; 1633 cm$^{-1}$,

NMR (in CDCl$_3$)δ: 3.18, 3H, singlet; 3.65, 3H, singlet; 3.80, 1H, quartet; 4.20, 2H, singlet; 6.86–8.22, 7H, multiplet.

EXAMPLE 20

Synthesis of 2-(5,6-dihydro-4-chloro-5-methyl-11-oxodibenz[b,e]azepin-2-yl)propionic acid Methyl 2-(5,6-dihydro-5-methyl-11-oxodibenz[b,e]azepin-2-yl)propionate (2.0 g), chloroform (50 ml) and N-chlorosuccinimide (1.4 g) were treated in the same manner as described in Example 9 to obtain the desired compound (1.7 g) as a yellow oily material.

IR, $\nu_{CO}^{Film}$: 1730 cm$^{-1}$; 1630 cm$^{-1}$,

MAS m/e: 343.

EXAMPLE 21

Synthesis of 5,6-dihydro-5-ethyl-11-oxodibenz[b,e]azepine-2-acetic acid

A mixed liquid of methyl 5,6-dihydro-5-ethyl-11-oxodibenz[b,e]azepine-2-acetate (0.9 g), sodium hydroxide (2 g), methanol (50 ml) and water (20 ml) was heated under refluxing for 2 hours. After the reaction, methanol was distilled off, and the remaining aqueous layer was washed with ether. The aqueous layer was treated with activated carbon powder, and a 5% sulfuric acid aqueous solution was added while cooling the layer with ice. The precipitated crystals were collected by filtration, washed in water, and vacuum-dried over $P_2O_5$ to obtain 5,6-dihydro-5-ethyl-11-oxodibenz[b,e]azepine-2-acetic acid (0.7 g), the desired compound, as yellow powdery crystals.

EXAMPLE 22

Synthesis of 5,6-dihydro-5-n-propyl-11-oxodibenz[b,e]azepine-2-acetic acid

A mixed liquid of methyl 5,6-dihydro-5-n-propyl-11-oxodibenz[b,e]azepine-2-acetate (0.5 g), sodium hydroxide (2 g), methanol (20 ml) and water (10 ml) was treated in the same manner as described in Example 21 to afford the desired compound (0.38 g) as yellow powdery crystals.

EXAMPLE 23

Synthesis of 5,6-dihydro-5-methyl-11-oxodibenz[b,e]azepine-2-acetic acid

A mixture of 5,6-dihydro-2-acetyl-5-methyl-11-oxodibenz[b,e]azepine (2.65 g), morpholine (10 ml) and sulfur powder (0.96 g) was heated under refluxing for 20 hours. The reaction mixture was poured into ice-water. The precipitated crystals were collected by filtration, washed in water, and dried to obtain its morpholide (4.2 g).

IR, $\nu^{KBr}$: 1630 cm$^{-1}$, 1110 cm$^{-1}$.

A mixture of the resulting crystals, potassium hydroxide (11.2 g), water (50 ml) and alcohol (50 ml) was heated under refluxing for 8 hours. After the reaction, alcohol was distilled off, and the residue was dissolved in water. The insoluble matter was removed by filtration. The filtrate was washed with ether, and adjusted to a pH of 5 wih 5% sulfuric acid to precipitate crystals. The crystals were collected by filtration, and dried to obtain the desired compound (2.2 g). m.p.: 194°–196° C. (recrystallied from acetone).

EXAMPLE 24

Synthesis of 5,6-dihydro-11-oxodibenz[b,e]azepine-2-acetic acid

A mixture of 5,6-dihydro-2-acetyl-11-oxodibenz[b,e]azepine (0.502 g), sulfur powder (0.256 g) and morpholine (1.74 g) was heated under refluxing for 4 hours. After the reaction, the reaction mixture was treated in the same manner as described in Example 23 to obtain its morpholide (0.80 g).

IR, $\nu^{KBr}$: 3320 cm$^{-1}$, 1630 cm$^{-1}$, 1107 cm$^{-1}$.

The resulting morpholide was heated under refluxing for 3.5 hours in a mixed liquid of ethyl alcohol (5 ml), potassium hydroxide (1 g) and water (5 ml). After the reaction, the reaction mixture was treated in the same manner as described in Example 23 to afford the desired compound (0.20 g).

m.p.: 132°–143° C.,

IR, $\nu^{KBr}$: 3340 cm$^{-1}$, 1700 cm$^{-1}$, 1630 cm$^{-1}$, 1610 cm$^{-1}$,

NMR (in CDCl$_3$)δ: 3.48, 2H, singlet; 4.15, 2H, doublet (J=6 Hz); 6.8, 1H, doublet (J=9 Hz); 7.1–7.7, 5H, multiplet; 7.79, 1H, doublet (J=2 Hz).

EXAMPLE 25

Synthesis of 5,6-dihydro-2-acetyl-5-methyl-11-oxodibenz[b,e]azepine

Acetyl chloride (8.5 g) was gradually added dropwise to a mixed liquid of 5,6-dihydro-5-methyl-11-oxodibenz[b,e]azepine (12 g), anhydrous aluminum chloride (21.5 g) and dried methylene chloride (200 ml) while stirring and cooling the liquid with ice. After the dropwise addition, the mixture was stirred for 30 minutes at room temperature, and was heated under refluxing for one hour. Immediately after the reaction, the reaction mixture was poured into a solution containing ice-water (1 kg) and conc. hydrochloric acid (50 ml) while stirring to separate the methylene chloride layer. This layer was washed with a 5% sodium hydrogencarbonate solution, then with water, and dried over magnesium sulfate. Thereafter, the solvent was distilled off, and the residue was recrystallized from methanol to afford the desired compound (13.2 g).

m.p.: 180.0°–181.0° C.,

IR, $\nu^{KBr}$: 1645 cm$^{-1}$, 1628 cm$^{-1}$,

NMR (in CDCl$_3$)δ: 2.61, 3H, singlet; 3.34, 3H, singlet; 4.32, 2H, singlet; 6.77–8.92, 7H, multiplet.

EXAMPLE 26

Synthesis of 5,6-dihydro-2-acetyl-11-oxodibenz[b,e]azepine 5,6-Dihydro-5-benzyl-11-oxodibenz[b,e]azepine (10.1 g), anhydrous aluminum chloride (16 g), acetyl chloride (8 g) and methylene chloride (100 ml) were treated in the same manner as described in Example 25 to obtain the desired compound (4 g).

m.p.: 205.5°–207.0° C. (recrystallized from acetone-benzene),

IR, $\nu^{KBr}$: 3320 cm$^{-1}$, 1660 cm$^{-1}$, 1615 cm$^{-1}$, 1605 cm$^{-1}$, 1260 cm$^{-1}$,

NMR (in CD$_3$)$_2$SO)δ: 2.5, 3H, singlet; 4.27, 2H, singlet; 6.89, 1H, doublet (J=9 Hz); 7.3–7.9, 5H, multiplet; 8.53, 1H, doublet (J=2 Hz).

EXAMPLE 27

Synthesis of 5,6-dihydro-2-acetyl-5-benzyl-11-oxodibenz[b,e]azepine 5,6-Dihydro-5-benzyl-11-oxodibenz[b,e]azepine (6.2 g), anhydrous aluminum chloride (6.07 g), acetyl chloride (4.87 g) and methylene chloride (60 ml) were treated in the same manner as described in Example 25 to obtain the desired compound (1.03 g).

m.p.: 163°–165° C. (recrystallized from benzene-petroleum ether),

IR, $\nu^{KBr}$: 1670 cm$^{-1}$, 1660 cm$^{-1}$, 1635 cm$^{-1}$, 1600 cm$^{-1}$,

NMR (in CDCl$_3$)δ: 2.6, 3H, singlet; 4.38, 2H, singlet; 4.80, 2H, singlet; 6.85, 1H, doublet (J=9 Hz); 7.0–8.0, 11H, multiplet; 8.8, 1H, doublet (J=2 Hz).

MAS m/e: 341.

EXAMPLE 28

Synthesis of ethyl 5,6-dihydro-11-oxodibenz[b,e]azepine-2-acetate

A mixture of 5,6-dihydro-11-oxodibenz[b,e]azepine-2-carboxylic acid (1.7 g), triethylamine (0.68 g), tetrahydrofuran (110 ml) and methylene chloride (85 ml) was cooled with ice, and a solution of ethyl chloroformate (2.19 g) in methylene chloride was added dropwise with stirring. The resultant mixture was stirred over night, and then, the solvent was distilled off. The residue was dissolved in methylene chloride, and the solution was washed in water and a saturated aqueous solution of sodium bicarbonate. The washed solution was dried over magnesium sulfate, and then, the solvent was distilled off. The resulting mixed acid anhydride was dissolved in methylene chloride and tetrahydrofuran, and the solution was added dropwise to a diazomethaneether solution under stirring and ice-cooling the latter solution. The mixture was allowed to stand for 3 days at room temperature, whereafter the solvent and the excess diazomethane were distilled off under reduced pressure. The residue obtained was dissolved in ethyl alcohol, and silver oxide was added. The mixture was heated under refluxing for 4 hours. After silver oxide was filtered off, the mother liquor was concentrated to give an oily material (2.8 g). The oily material was purified by thin-layer chromatography, and recrystallized from methanol to afford the desired compound (0.333 g).

m.p.: 99°–101° C.,

IR, $\nu^{KBr}$: 3380 cm$^{-1}$, 1730 cm$^{-1}$, 1630 cm$^{-1}$, 1610 cm$^{-1}$,

NMR (in CDCl$_3$)δ: 1.25, 3H, triplet (J=7 Hz); 3.52, 2H, singlet; 4.13, 2H, quartet (J=7 Hz); 4.19, 2H, singlet; 5.3, 1H, broad; 6.53, 1H, doublet (J=9 Hz); 7–7.8, 5H, multiplet.

MAS m/e: 295.

The starting 5,6-dihydro-11-oxodibenz[b,e]azepine-2-carboxylic acid had been synthesized in the following manner:

A mixture of 5,6-dihydro-2-bromo-6,11-dioxodibenz[b,e]azepine (151 g), cuprous cyanide (49 g) and dimethylformamide (1.1 liters) was heated under refluxing for 8.5 hours. Then, the reaction mixture was cooled, and poured into a solution containing ferric chloride (200 g), conc. hydrochloric acid (50 ml) and water (500 ml) under stirring. The precipitated crystals were collected by filtration, washed with hydrochloric acid, and further washed thoroughly in water. Then, the crystals were dried at 60°–80° C. and dissolved in dimethylformamide (700 ml) with heating. The solution was filtered on heating, concentrated to 500 ml, and allowed to stand with the addition of dioxane (300 ml). The precipitated crystals were collected by filtration, washed with dioxane, then with n-hexane, and dried to obtain 5,6-dihydro-2-cyano-6,11-dioxodibenz[b,e]azepine (75 g).

m.p.: above 300° C.,

IR, $\nu^{KBr}$: 2220 cm$^{-1}$, 1660 cm$^{-1}$, 1604 cm$^{-1}$,

MAS m/e: 248.

5,6-Dihydro-2-cyano-6,11-dioxodibenz[b,e]azepine (25 g) obtained above was mixed with dimethylaniline (7.5 ml) and phosphorus oxychloride (200 ml), and the mixture was heated under refluxing for 8 hours. After cooling of the mixture, the excess phosphorus oxychloride was distilled off under reduced pressure. The residue was given xylene and distilled again under reduced pressure. The residue was dissolved in benzene, and the solution was washed with ice-water. The washed solution was further washed in water, then dried over magnesium sulfate, and was concentrated. The concentrate was allowed to cool, affording 2-cyano-6-chloro-11-oxodibenz[b,e]azepine (18 g).

m.p.: 217°–220° C.,

IR, $\nu^{KBr}$: 2220 cm$^{-1}$, 1660 cm$^{-1}$, 1620 cm$^{-1}$, 1590 cm$^{-1}$, 760 cm$^{-1}$,

MAS m/e: 266.

The resulting 2-cyano-6-chloro-11-oxodibenz[b,e]azepine (17.4 g) and triethylamine (9 g) were dissolved in dioxane (840 ml), and the solution was catalytically hydrogenated for 17 hours at room temperature at a hydrogen pressure of 4 kg/cm$^2$ with 10% palladium-carbon powder (2 g) as a catalyst. After the hydrogenation, the catalyst was filtered off, and the filtrate was concentrated at reduced pressure. The concentrate was purified by silica gel chromatography, and recrystallized from acetone to obtain 5,6-dihydro-2-cyano-11-oxodibenz[b,e]azepine (7.06 g).

m.p.: 235.0°–236.5° C.

IR, $\nu^{KBr}$: 3310 cm$^{-1}$, 2200 cm$^{-1}$, 1620 cm$^{-1}$,

NMR (in CDCl$_3$)δ: 4.35, 2H, doublet (J=6 Hz); 5.7, 1H, broad; 6.7, 1H, doublet (J=9 Hz); 7.15-7.8, 5H, multiplet; 8.45, 1H, doublet (J=3 Hz), MAS m/e: 234.

The resulting 5,6-dihydro-2-cyano-11-oxodibenz[b,e]azepine (6.41 g) was heated under refluxing for 2.5 hours in a solution containing conced sulfuric acid (40 ml) and water (40 ml). After its cooling, the system was poured into water to precipitate crystals. The crystals were collected by filtration, washed in water, and dried. The dried crystals were heated under refluxing for 3 hours in a solution containing methanol (600 ml) and conc. sulfuric acid (20 ml). The resultant solution was concentrated, and poured into ice-water. Water was added until the total volume came up to about 1 liter. The precipitated crystals were collected by filtration, washed in water, and dissolved in chloroform. The solution was further washed in water and dried. Chloroform was distilled off to give crystals. The crystals were recrystallized from methyl acetate to yield methyl 5,6-dihydro-11-oxodibenz[b,e]azepine-2-carboxylate (2.25 g). These crystals were heated under refluxing for 2.5 hours in a mixed liquid of methanol (60 ml), sodium hydroxide (3 g) and water (60 ml). After its cooling, the reaction mixture was concentrated, and 1 N sulfuric acid was added. The precipitated crystals were collected by filtration, and washed in water to afford 5,6-dihydro-11-oxodibenz[b,e]azepine-2-carboxylic acid (1.7 g) having a melting point of higher than 300° C.

IR, $\nu^{KBr}$: 3340 cm$^{-1}$, 1680 cm$^{-1}$, 1625 cm$^{-1}$,

NMR (in (CD$_3$)$_2$SO)δ: 4.25, 2H, doublet (J=6 Hz); 6.9, 1H, doublet (J=9 Hz); 7.3–8.3, 5H, multiplet; 8.55, 1H, doublet (J=3 Hz).

EXAMPLE 29

Synthesis of 5,6-dihydro-11-oxodibenz[b,e]azepine-2-acetic acid

A mixture of ethyl 5,6-dihydro-11-oxodibenz[b,e]azepine-2-acetate (0.333 g), methanol (20 ml) sodium hydroxide (1 g) and water (20 ml) was heated under refluxing for 3 hours. After removal of the solvent by distillation, water was added to the mixture, and then, 5% sulfuric acid was added. The precipitated crystals were collected by filtration, washed in water, and dried to obtain 5,6-dihydro-11-oxodibenz[b,e]azepine-2-acetic acid (0.206 g). m.p.: 135°–145° C.

EXAMPLE 30

Synthesis of ethyl 5,6-dihydro-11-oxodibenz[b,e]azepine-2-acetate 5,6-Dihydro-11-oxodibenz[b,e]azepine-2-acetic acid was esterified with ethanol-sulfuric acid in a customary manner to obtain ethyl 5,6-dihydro-11-oxodibenz[b,e]azepine-2-acetate.

m.p.: 98°–100° C. (recrystallized from ether-n-hexane).

Examples of the production of pharmaceutical preparations containing the compound of the present invention are given below.

EXAMPLE A: TABLET

Tablets containing 50 mg and 100 mg of the active ingredient a tablet may be prepared as follows:

| Formula 1-a 50 mg tablet | mg/tablet |
|---|---|
| 5,6-Dihydro-5-methyl-11-oxodibenz[b,e]azepine-2-acetic acid | 50 |
| Lactose | 92.2 |
| Starch | 44.8 |
| Calcium carboxymethyl cellulose | 10 |
| Talc | 2 |
| Magnesium stearate | 1 |
|  | 200.0 |
| Formula 1-b 100 mg tablet | mg/tablet |
| 5,6-Dihydro-5-methyl-11-oxodibenz[b,e]azepine-2-acetic acid | 100 |
| Lactose | 42.2 |
| Starch | 44.8 |
| Calcium carboxymethyl cellulose | 10 |
| Talc | 2 |
| Magnesium stearate | 1 |
|  | 200.0 |

Crystals of 5,6-dihydro-5-methyl-11-oxodibenz[b,e]azepine-2-acetic acid were pulverized to less than 70 microns, and lactose and starch were added, followed by thorough mixing. 10% starch paste was added to the mixed powder, and the system was mixed to prepare granules with stirring. After dry granulation, the particle size of granules was maintained uniform at about 840 microns. Talc and magnesium stearate were mixed with the granules, and tablets were formed from the granules.

EXAMPLE B: CAPSULE

| Formula 2-a 50 mg capsule | mg/capsule |
|---|---|
| 5,6-Dihydro-5-methyl-11-oxodibenz[b,e]azepine-2-acetic acid | 50 |
| Starch | 30 |
| Lactose | 27.8 |
| Magnesium stearate | 2.2 |
|  | 110.0 mg |
| Formula 2-b 100 mg capsule | mg/capsule |
| 5,6-Dihydro-5-methyl-11-oxodibenz[b,e]azepine-2-acetic acid | 100 |
| Starch | 60 |
| Lactose | 55.6 |
| Magnesium stearate | 4.4 |
|  | 220.0 mg |

5,6-Dihydro-5-methyl-11-oxodibenz[b,e]azepine-2-acetic acid was finally pulverized, and starch, lactose and magnesium stearate were added to the pulverized substance. The system was mixed well, and the mixture corresponding to 50 mg of the main ingredient was introduced to fill No. 5 capsules, while the mixture corresponding to 100 mg of the main ingredient was introduced to fill No. 2 capsules.

EXAMPLE C: SUSPENDED INJECTION

| | |
|---|---|
| 5,6-Dihydro-5-methyl-11-oxodibenz[b,e]azepine-2-acetic acid | 20 mg |
| Methyl cellulose | 2.0 mg |
| Benzyl alcohol | 9.0 mg |
| Methyl p-hydroxybenzoate | 1.8 mg |
| Propyl p-hydroxybenzoate | 0.2 mg |
| Tween 20 | 0.5 mg |
| Sodium chloride | 9.0 mg |
| | Total volume 1 ml by addition of water for injection. |

The method for preparing the suspended injection is described in detail below.

Water for injection (10 liters) was heated to 50°–60° C., and methyl cellulose (20 g), sodium chloride (90 g) and Tween 20 (5 g) were dissolved in the water with stirring. To the solution was added dropwise a solution of methyl p-hydroxybenzoate (18 g) and propyl p-hydroxybenzoate (2 g) dissolved in benzyl alcohol (90 g), and the system was mixed well. After the components were completely dissolved, the resulting solution was adjusted to a pH of 7.0 with diluted hydrochloric acid or dilute aqueous sodium hydroxide. This solution was put in an autoclave, and sterilized for 20 minutes at 120° C.

5,6-Dihydro-5-methyl-11-oxodibenz[b,e]azepine-2-acetic acid (200 g) was dissolved in 90% ethanol (4 liters) with heating, and the solution was filtered aseptically through a Millipore Filter (HA). Then, the filtrate was introduced into water for injection (10 liters) with stirring. Fine crystals which precipitated were separated by filtration, and washed thoroughly in water for injection. To the washed fine crystals was added the sterilized dispersion medium (about 8 liters) that had been prepared above. An ultrasonic homogenizer was used to disperse the crystals well. Then, the rest of said sterilized dispersion medium was added until the total volume reached 10 liters.

What we claim is:

1. A compound of the formula

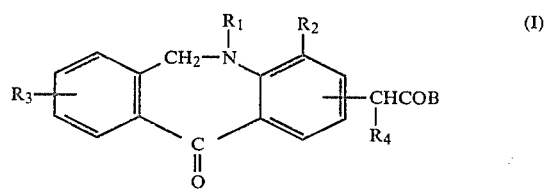

wherein $R_1$ represents alkyl of up to 6 carbon atoms, $R_2$ represents hydrogen, halogen or nitro, $R_3$ represents hydrogen or halogen, and $R_4$ represents hydrogen or alkyl of up to 6 carbon atoms; and B represents hydroxyl, $-OR'_{104}$ or $-NHR'_{105}$ wherein $R'_{104}$ is alkyl of up to 6 carbon atoms, mono- or di-hydroxy alkyl of up to 6 carbon atoms, alkoxy-alkyl in which each of the alkoxy and alkyl groups have up to 6 carbon atoms, or 2,2-dimethyl-1,3-dioxolan-5-yl alkyl of up to 6 carbon atoms in the alkyl group, and $R'_{105}$ is hydrogen, hydroxyl, amino, alkyl of up to 6 carbon atoms or hydroxyalkyl of up to 6 carbon atoms, or a pharmaceutically acceptable salt of the compound wherein B is hydroxyl.

2. A salt of claim 1 which is an alkali metal salt, an alkaline earth metal salt, an aluminum salt or an ammonium salt.

3. A compound of claim 1 wherein B represents hydroxyl, —OR''$_{104}$ or —NHR''$_{105}$ in which R''$_{104}$ is methyl, ethyl, hydroxyethyl or 2,2-dimethyl-1,3-dioxolan-5-yl methyl, and R''$_{105}$ is hydrogen, methyl or hydroxyl; and the salt is an alkali metal salt, an alkaline earth metal salt or an aluminum salt.

4. A compound of claim 1, which is a compound of the formula

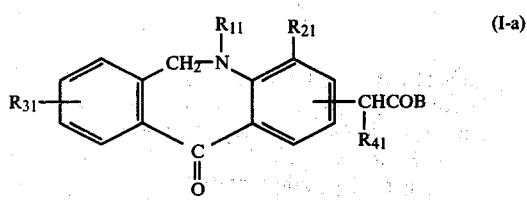

wherein $R_{11}$ is alkyl of 1 to 4 carbon atoms, $R_{21}$ is hydrogen, chlorine, bromine or nitro, $R_{31}$ is hydrogen, chlorine or bromine, $R_{41}$ is hydrogen or methyl, and B is as defined in claim 56; or a pharmaceutically acceptable salt of the compound wherein B is hydroxyl.

5. A salt of claim 4 which is an alkali metal salt, in alkaline earth metal salt, in aluminum salt or an ammonium salt.

6. A compound of claim 1, which is a compound of the formula

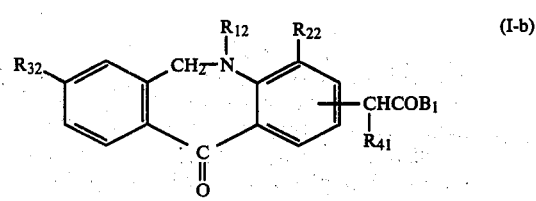

wherein $R_{12}$ is methyl, ethyl or n-propyl, $R_{22}$ is hydrogen, chlorine or bromine, $R_{32}$ is hydrogen or chlorine, $R_{41}$ is hydrogen or methyl, and $B_1$ represents hydroxyl, —OR''$_{104}$ or —NHR''$_{105}$ in which R''$_{104}$ is methyl, ethyl, hydroxyethyl or 2,2-dimethyl-1,3-dioxolan-5-yl methyl, and R''$_{105}$ is hydrogen, methyl or hydroxyl; or a pharmaceutically acceptable salt of the compound wherein $B_1$ is hydroxyl.

7. A salt of claim 6 which is an alkali metal salt, an alkaline earth metal salt or an aluminum salt.

8. 5,6-Dihydro-5-methyl-11-oxodibenz[b,e]azepine-2-acetic acid according to claim 1.

9. 5,6-Dihydro-5-ethyl-11-oxodibenz[b,e]azepine-2-acetic acid according to claim 1.

10. 5,6-Dihydro-5-methyl-11-oxodibenz[b,e]azepine-3-acetic acid according to claim 1.

11. Methyl 5,6-dihydro-5-methyl-11-oxodibenz[b,e]azepine-2-acetate according to claim 1.

12. Hydroxyethyl 5,6-dihydro-5-methyl-11-oxodibenz[b,e]azepine-2-acetate according to claim 1.

13. 2,2-Dimethyl-1,3-dioxolan-5-yl methyl 5,6-dihydro-5-methyl-11-oxodibenz[b,e]azepine-2-acetate according to claim 1.

14. A compound of claim 1 wherein $R_1$ represents alkyl of 1 to 4 carbon atoms.

15. A compound of claim 1 or 14 wherein $R_2$ represents hydrogen, chlorine, bromine or nitro.

16. A compound of claim 15 wherein the group

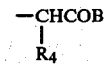

is located at the 2- or 3-position of the dibenz[b,e]azepine ring.

17. A compound of claim 15 wherein $R_3$ represents hydrogen or halogen located at the 8- or 9-position of the dibenz[b,e]azepine ring.

18. A compound of claim 15 wherein $R_4$ represents hydrogen or methyl.

19. A compound of claim 1 or 14 wherein $R_3$ represents hydrogen or halogen located at the 8- or 9-position of the dibenz[b,e]azepine ring.

20. A compound of claim 19 wherein $R_4$ represents hydrogen or methyl.

21. A compound of claim 19 wherein the group

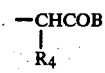

is located at the 2- or 3-position of the dibenz[b,e]azepine ring.

22. A compound of claim 1 or 14 wherein $R_4$ represents hydrogen or methyl.

23. A compound of claim 22 wherein the group

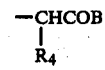

is located at the 2- or 3-position of the dibenz[b,e]azepine ring.

24. A compound of claim 1 or 14 wherein the group

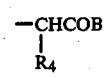

is located at the 2- or 3-position of the dibenz[b,e]azepine ring.

25. A compound of the formula

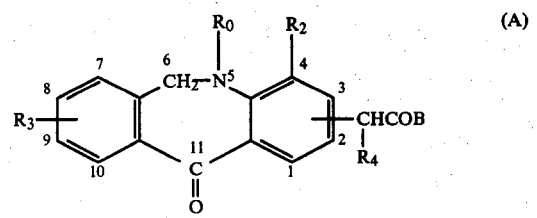

wherein $R_o$ represents hydrogen or alkyl of up to 6 carbon atoms, $R_2$ represents hydrogen, halogen or nitro, $R_3$ represents hydrogen or halogen, and $R_4$ represents hydrogen or alkyl of up to 6 carbon atoms, and when $R_o$ represents hydrogen $R_2$, $R_3$ and $R_4$ all represent hydrogen and the group

—CHCOB
|
R4 is present at the 2-position; and B represents hydroxyl, —OR'$_{104}$ or —NHR'$_{105}$ wherein R'$_{104}$ is alkyl of up to 6 carbon atoms, mono- or di-hydroxy alkyl of up to 6 carbon atoms, alkoxyalkyl in which each of the alkoxy and alkyl groups have up to 6 carbon atoms, or 2,2-dimethyl-1,3-dioxolan-5-yl alkyl of up to 6 carbon atoms in the alkyl group, and R'$_{105}$ is hydrogen, hydroxyl, amino, alkyl of up to 6 carbon atoms or hydroxy alkyl of up to 6 carbon atoms, or a pharmaceutically acceptable salt of the compound wherein B is hydroxyl.

26. A salt of claim 25 which is an alkali metal salt, an alkaline earth metal salt, an aluminum salt or an ammonium salt.

27. A compound of the formula

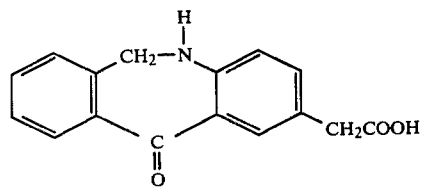

or an alkali metal salt, an alkaline earth metal salt, an aluminum salt or a $C_1$–$C_6$ alkyl ester of said compound.

28. A compound of the formula

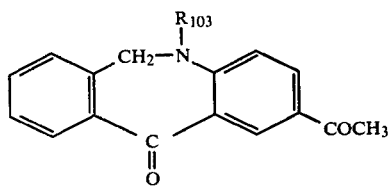

wherein R$_{103}$ is hydrogen, alkyl of up to 6 carbon atoms, or aralkyl or 7 to 20 carbon atoms.

29. A compound of claim 28 wherein R$_{103}$ represents hydrogen, alkyl of up to 6 carbon atoms, benzyl, 4-methoxybenzyl or diphenylmethyl.

30. A pharmaceutical composition having analgesic and/or anti-inflammatory activity which comprises,
(A) as an active ingredient, a therapeutically effective amount of a compound selected from the group consisting of (1) a compound of the formula

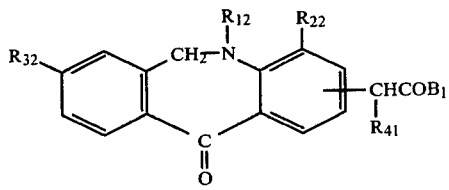

wherein R$_{12}$ is methyl, ethyl or n-propyl, R$_{22}$ is hydrogen, chlorine or bromine, R$_{32}$ is hydrogen or chlorine, R$_{41}$ is hydrogen or methyl, and B$_1$ represents hydroxyl, —OR"$_{104}$ or —NHR"$_{105}$ in which R"$_{104}$ is methyl, ethyl, hydroxyethyl or 2,2-dimethyl-1,3-dioxolan-5-yl methyl, and R"$_{105}$ is hydrogen, methyl or hydroxyl; (2) an alkali metal salt, an alkaline earth metal salt or an aluminum salt of said compound of formula I-b wherein B$_1$ is hydroxyl; (3) a compound of the formula

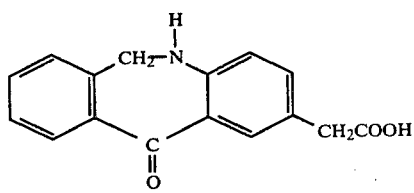

an alkali metal, alkaline earth metal or aluminum salt of said compound of formula II; and (5) an alkyl ester of said compound of formula II in which the alkyl group contains up to 6 carbon atoms, and
(B) a non-toxic pharmaceutically acceptable carrier or excipient.

* * * * *